United States Patent
Zitvogel et al.

(10) Patent No.: US 6,685,911 B1
(45) Date of Patent: Feb. 3, 2004

(54) SENSITIZATION PROCESS FOR ANTIGEN-PRESENTING CELLS AND MEANS FOR IMPLEMENTING THE PROCESS

(75) Inventors: Laurence Zitvogel, Paris (FR); Graça Raposo, Paris (FR); Armelle Regnault, Paris (FR); Sebastian Amigorena, Paris (FR)

(73) Assignees: Institut National de la Sante et de la Recherche Medicale, Paris (FR); Institut Gustave Roussy, Villejuif (FR); Centre National de la Recherche Scientifique, Paris (FR); Institut Curie, Paris (FR)

( * ) Notice: Subject to any disclaimer, the term of this patent is extended or adjusted under 35 U.S.C. 154(b) by 0 days.

(21) Appl. No.: 09/267,370

(22) Filed: Mar. 15, 1999

Related U.S. Application Data

(63) Continuation of application No. PCT/FR98/01431, filed on Jul. 3, 1998.

(30) Foreign Application Priority Data

Jul. 16, 1997 (FR) .............................. 97 09007
Feb. 6, 1998 (FR) .............................. 98 01437

(51) Int. Cl.$^7$ ........................ A61K 51/00; A61K 39/00; A61K 39/38; A61M 36/14; C12P 21/04
(52) U.S. Cl. .................. 424/1.21; 424/184.1; 435/70.1; 435/377
(58) Field of Search .............................. 424/93.1, 277.1, 424/1.21, 184.1; 530/350; 435/325, 70.1, 377

(56) References Cited

FOREIGN PATENT DOCUMENTS

WO     WO 97/05900     2/1997

OTHER PUBLICATIONS

Kleijmeer et al, J. Immunol., 1995, 154: 5715–5724.*
Mayordomo et al, Nature Med., 1995, 1(12): 1297–1301.*
Rapso et al., "B Lymphocytes Secrete Antigen–presenting Vesicles," *J. Exp. Med.* 183: 1161–1172 (1996).
Amigorena et al., "Transient accumulation of new class II MHC molecules in a novel endocytic compartment in B lymphocytes," *Nature* 369:113–120 (1994).
Tulp et al., "Isolation and characterization of the intracellular MHC class II compartment," *Nature* 369: 120–126 (1994).
Gruenberg et al., "Characterization of the Early Endosome and Putative Endocytic Carrier Vesicles In Vivo and With an Assay of Vesicle Fusion In Vitro," *J. Cell. Biol.* 108:1301–1316 (1989).
Trams et al., "Exfoliation of Membrane Ecto–Enzymes in the Form of Micro–Vesicles," *Biochimica et Biophysica Acta* 645: 63–70 (1981).
Bernhard et al., "Generation of Immunostimulatory Dendritic Cells from Human CD34+ Hermatopoietic Progenitor Cells of the Bone Marrow and Peripheral Blood," *Cancer Res.* 55: 1099–1104 (1995).
Romani et al., "Proliferating Dendritic Cell Progenitors in Human Blood," *J. Exp. Med.* 180: 83–93 (1994).
Hsu et al., "Vaccination of patients with B–cell lymphoma using autologous antigen–pulsed dendritic cells," *Nature Med.* 2(1): 52–58 (1996).
Zitvogel et al., "Eradication of established murine tumors using a novel cell–free vaccine: dendritic cell–derived exosomes," *Nature Med.* 4(5): 594–600 (1998).

* cited by examiner

*Primary Examiner*—Peter Paras
(74) *Attorney, Agent, or Firm*—Preston Gates Ellis & Rouvelas Meeds LLP

(57) ABSTRACT

The object of the invention is a novel sensitization process for antigen-presenting cells, novel means for implementing the process and novel membrane vesicles possessing immunogenic potency. The invention relates in particular to texosomes (vesicles derived from tumor cells) and dexosomes (vesicles derived from dendritic cells loaded or not with antigens), and their use for the vectorization and presentation of antigens in vitro or in vivo as well as in methods or compositions for the treatment of cancers and infectious, parasitic or autoimmune diseases in particular.

5 Claims, 22 Drawing Sheets

Figure 1A:
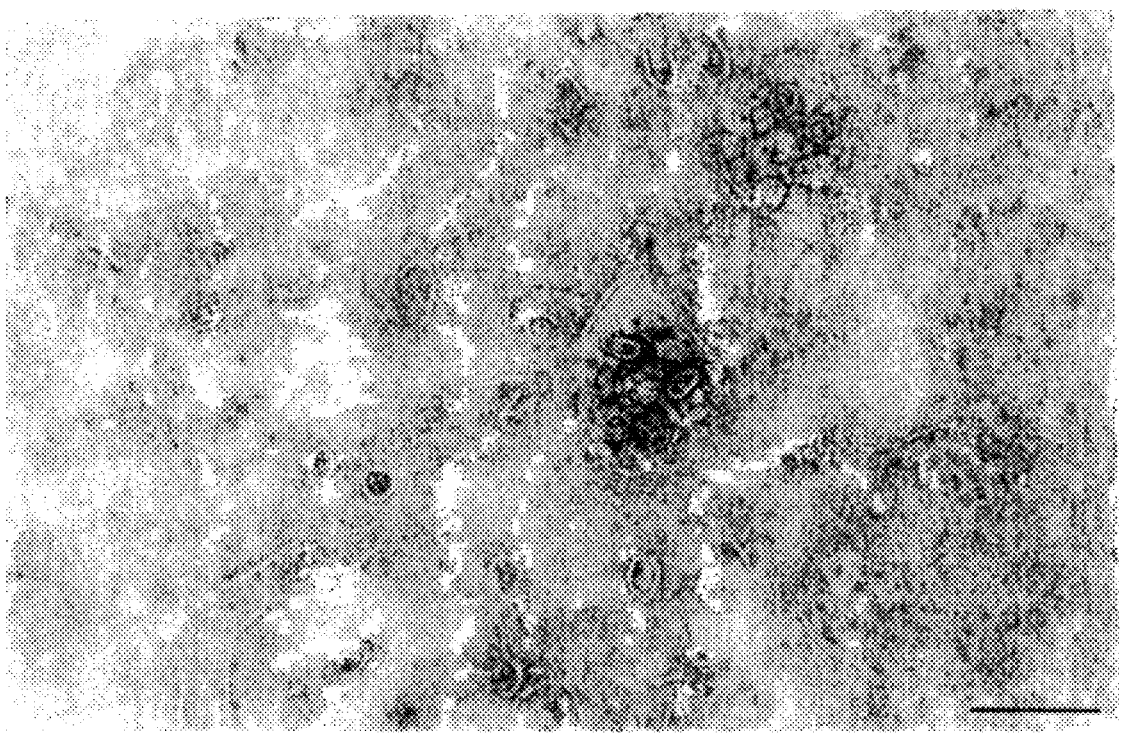

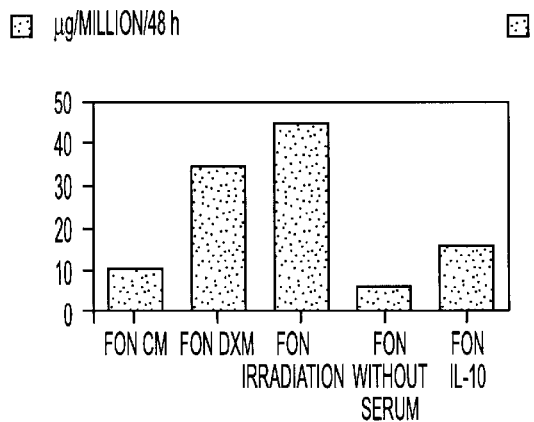
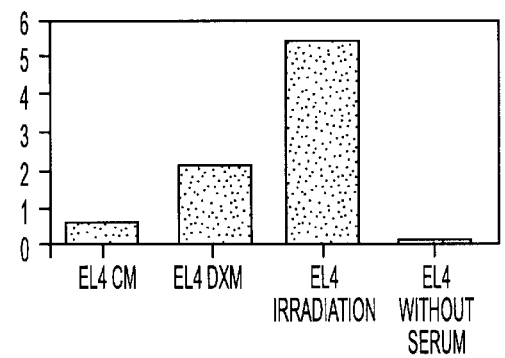
FIG. 8A
FIG. 8B
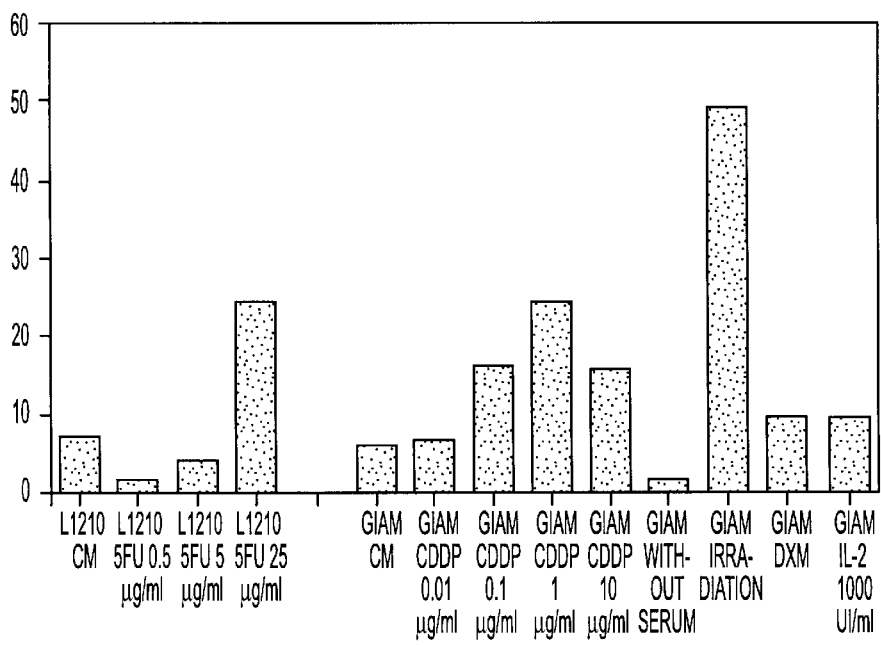
FIG. 8C

SEQUENCE LISTING

```
<160> NUMBER OF SEQ ID NOS: 1

<210> SEQ ID NO 1
<211> LENGTH: 9
<212> TYPE: PRT
<213> ORGANISM: Unknown Organism
<220> FEATURE:
<223> OTHER INFORMATION: Description of Unknown Organism: Peptide
      derived from MART-1

<400> SEQUENCE: 1

Ala Ala Gly Ile Gly Ile Leu Thr Val
  1               5
```

SENSITIZATION PROCESS FOR ANTIGEN-PRESENTING CELLS AND MEANS FOR IMPLEMENTING THE PROCESS

This application is a continuation of application Ser. No. PCT/FR98/01431, filed Jul. 3, 1998.

The object of the invention is a novel process for sensitizing antigen-presenting cells, novel means for the implementation of the process and novel membrane vesicles having an immunogenic potency.

Since the demonstration of the existence of CD8+ cytotoxic T lymphocytes specific for tumor antigens presented in the context of class I molecules (Rosenberg et al., 1996; Boon, 1992), several laboratories have been able to show that anti-tumor immuno-therapy is an efficacious therapeutic strategy in animal models (Pardoll, 1995). The principle of immunotherapy is to induce an effective immune response against specific tumor antigens. Up to the present, it has been possible to carry this out in different ways. First, tumor cells expressing recombinant co-stimulatory molecules and/or immunomodulatory cytokines are capable of stimulating anti-tumor responses capable of eradicating solid tumors in vivo (Zitvogel et al., 1996 {a}). Similarly, peptide derivatives of tumor antigens (or exogenous antigens expressed in tumor cells) injected in different chemical forms including the use of liposomes or viruses (adenovirus or poxvirus, for example) as vectors are capable of causing tumors to regress. Finally, professional antigen-presenting cells, such as dendritic cells sensitized with peptides derived from tumor antigens, reinjected in vivo induce potent anti-tumor responses as well as the regression of solid tumors established in mice (Mayordomo et al., 1995).

Immunotherapy based on the use of dendritic cells has been able to show its efficacy in the studies conducted in the mouse. As a result, this therapy has recently been transposed to the clinic. In the Unites States, trials are presently underway to demonstrate that dendritic cells loaded with tumor peptides significantly increase the frequency of specific cytotoxic T lymphocytes (CTL).

A first limitation to this approach is the sensitization of the dendritic cells with peptides derived from tumor antigens. In fact, in the majority of tumors specific antigens have not been identified. Antigens specific to the tumors are only known in cases of tumors induced by viruses (carcinoma of the uterine cervix), in cases of melanoma (self antigens, mutated antigens, differentiation antigens) or in a small percentage of breast tumors (oncogenes or products of tumor suppressor genes having undergone mutations). However, the direct implication of these peptides or tumor antigens in the elimination of the tumors in man remains to be demonstrated. Novel sensitization methods of the antigen-presenting cells such as dendritic cells thus prove to be necessary. The object of these methods is to induce specific anti-tumor responses in the context of class I and class II molecules of the MHC.

Most of the sensitization methods of dendritic cells at present use peptides corresponding to epitopes presented in combination with the class I molecules and identified in tumor cells by means of CTL clones specific for the tumor. However, these methods are probably not optimal since they do not take into account epitopes recognized in the context of the class II molecules which are critical for the proliferation of the helper T lymphocytes necessary for obtaining optimal cytotoxic responses. Furthermore, epitopes presented by the tumor cells and those presented by antigen-presenting cells (as for example the dendritic cells) are probably not the same. Finally, tumor peptides recognized by the CTL are only available in the case of a small percentage of patients having molecules of the appropriate class I haplotype.

The ideal sensitization method, one which would be applicable to any tumor with a minimal risk of immunoselection, must not be limited to a small number of identified tumor antigens. Similarly, such a method ought to make use of intact protein antigens rather than peptides in order to enable the dendritic cell to prepare them and to present the adequate combination of peptides in combination with the class I and class II molecules, and do so for any individual.

Recently, Gilboa and collaborators (Boczkowsky et al., 1996) have been able to show that messenger RNAs prepared from tumors biopsies loaded in the dendritic cells may have an in vivo anti-tumor effect. However, the RNAs are very unstable and the quantity of potentially interesting RNA compared with the total RNA is probably very low. Zitvogel et al. (Zitvogel et al., 1996 {b}) have shown that tumor peptides prepared from an acidic tumor eluate (acidic peptide eluate: APE) may be used to load dendritic cells. These cells thus loaded, once injected, have the capacity to cause tumors to regress. However, in the case of tumors which do not express tumors of class I (which represent the majority of metastatic human tumors) or in the case of tumors which may not be dissociated in a cellular suspension, the approach using the acidic eluates is not very efficacious and not reproducible.

A second limitation to immunotherapy based on the use of dendritic cells is linked to the phenotypic changes which may occur when these cells are maintained in culture or subjected to different treatments. This may in fact lead to cell populations which are not very homogeneous and inadequately characterized for therapeutic use.

Hence there exists a real need to improve the methods for sensitizing antigen-presenting cells in order to enhance the efficacy of these approaches and to broaden their applications as well as to develop novel means for the vectorization of antigens and other molecules.

The present invention provides solutions to these questions. The object of the present invention is in fact to provide novel methods for sensitizing antigen-presenting cells, in particular dendritic cell, as well as for the identification, isolation and characterization of the novel membrane vesicles having remarkable immunogenic properties.

One of the features of the invention is more particularly to provide a novel reproducible process for sensitizing antigen-presenting cells by tumor antigens.

Another feature of the invention is to provide a novel reproducible process for sensitizing antigen-presenting cells by tumor antigens, in which it is not necessary that the tumor antigens are known.

Another feature of the invention is to provide the means which make it possible to set up a library of tumor antigens.

Another feature of the invention resides in lipid membrane vesicles produced by the tumor cells or by the dendritic cells and endowed with immunogenic properties as well as their use for the production of antigen libraries, the sensitization of antigen-presenting cells or the vectorization of antigens, in particular in the context of immunotherapeutic approaches.

In this respect a first object of the invention relates to a vesicle derived from tumor cells having the following characteristics:
- it is freed from its natural environment,
- it comprises a lipid bilayer (designated by "surface") which surrounds a cytosolic fraction, and optionally, it exhibits on its surface molecules of class I of the major histocompatibility complex (MHC) and/or of class II of the major histocompatibility complex (MHC), optionally loaded with antigenic peptides and/or adhesion molecules and/or lymphocytic costimulatory molecules, and/or, it contains in its cytosolic fraction tumor antigen molecules and/or immunomodulators and/or chemo-attractors and/or hormones and/or nudeic acids.

The secretion of the vesicles by cells is a phenomenon described in the prior art (reticulocytes, B lymphocytes, macrophages). These vesicles are usually designated by the generic term "exosome" which reflects their mechanism of production by exocytosis of internal vesicles. However, the physiological role of these vesicles has not been really established. Furthermore, the structural characteristics, properties and functions of these vesicles vary depending on the cell type from which they are derived.

Unexpectedly, the inventors have now demonstrated that tumor cells are capable of secreting vesicles exhibiting particularly interesting immunogenic properties. These vesicles usually correspond to an internal vesicle contained in an endosome of a tumor cell and secreted by said tumor cell subsequent to the fusion of the external membrane of said endosome with cytoplasmic membrane of above-mentioned tumor cell. Owing to this mechanism of formation, their cellular origin and their original functional properties and characteristics, these vesicles are designated in what follows by the term <<texosome>>.

The expression "freed from its natural environment" signifies that the vesicle is separated physically from the cell from which it is derived or even that it is partially isolated or purified. Usually, the vesicle is thus produced by the cell by means of exocytosis, then partially isolated and purified so as to produce an enriched composition. This expression may also signify that not only the vesicle was secreted by the cell at the moment of fusion of the multivesicular endosomes with the plasma membrane, but that it is no longer surrounded by soluble elements which are in the lumen of the endosome, or that it lacks intact cells. The expression "derived from a tumor cell" signifies that the vesicle possesses structural elements of a tumor cell. This vesicle is usually "derived" from a tumor cell in the sense in that it is produced, at least in part, then released by a tumor cell, at a given stage of its development.

According to an advantageous embodiment of the invention, the texosomes of the invention exhibit MHC molecules loaded with antigenic peptides and/or express adhesion molecules and/or express lymphocytic costimulatory molecules, but lack in their cytosolic fraction tumor antigenic molecules and immuno-modulators and nucleic acids.

According to another advantageous embodiment the texosomes of the invention are such that the molecules of the MHC are "empty", i.e. not loaded with antigenic peptides and the texosomes comprise in their cytosolic fraction tumor antigenic molecules, immunomodulators and/or nucleic acids. Texosomes having empty MHC molecules may be obtained either from tumor cells exhibiting for example a deficiency of the peptide transporter (TAP) or by washing of texosomes or tumor cells in order to eluate the peptides associated with the molecules of the MHC.

According to an advantageous embodiment of the invention, the texosomes of the invention are such that the molecules of the MHC are loaded with antigenic peptides and/or express adhesion molecules and/or express lymphocytic costimulatory molecules and the texosomes contain in their cytosolic fraction tumor antigenic molecules, immunomodulators and/or nudeic acids.

The term "tumor cells" embraces in a general manner any cell derived from a tumor, for example a solid or liquid tumor, as well as the cells transformed or immortalized in vitro. Preferably, it refers to a solid, ascitic or hematopoietic tumor.

As examples, mention may be made of the cancer cells of the malignant melanoma type (derived from primary lines established "ex vivo" or even dissociated cells derived from the operating theatre) which express at their surface peptides like MART-1/Melan-A in the context of MHC class 1, HLA-A 02-01, and containing the protein antigen MART-1.

Mention may also be made of cells derived from renal cancer (clear cell adenocarcinoma) or leukemias the cells of which express specific translocation products.

Thus, the antigenic peptides likely to load the molecules of the MHC are derived from the following antigens for example: those derived from melanomas such as: MART-1, tyrosinase, MAGE-1/2/3, P53 (in different tumors) or HER2/Neu, PSA, CEA or also PSMA. Other tumor antigens are cited for example in the article by Rosenberg (Immunology Today 18 (1997) 175) incorporated into the present description as a reference.

More generally, mention may be made of fusion/translocation products, products of oncogenes or anti-oncogenes, or even differentiation antigens or peptides of self or mutated peptides.

By lymphocytic costimulatory molecules is meant for example molecules which give to the T lymphocytes additional signals to those given on interaction of the complexes molecule of class I and class II—peptide with the T cell receptor.

As examples, mention may be made of:

CD80, CD86, ICAM, LFA, CD40, certain members of the TNF R family and adhesion or chemo-attraction molecules (permitting contact between the professional antigen-presenting cell and the effector lymphocytes, or the intracellular transport/specific localization ("trafficking/homing") of other cells to the vaccinal or inflammatory site.

The tumor antigenic molecules contained in the cytosol or presented by the texosomes derive from proteins expressed selectively and/or abundantly by the tumor cells.

The immunomodulators which may be present in the cytosol of the texosomes are, for example TNF-α, or interleukin 1, or interleukin 15, or C-CR (chemokines).

The nudeic acids likely to be present in the cytosol of the texosomes are derived from the tumor cell itself. These nucleic acids are found in the cytosol of the texosomes as a direct consequence of their mechanism of formation. They may also be heterologous nucleic acids.

More special characteristics of the texosomes of the invention are the following:

they are small membrane vesicles of about 60 to 100 nm, most often about 60 to 90 nm, in particular 60 to 80 nm, secreted by the tumor cells, they possess molecules usually present in the endosomes, they contain tumor antigens, like for example MART-1 in the case of melanoma cells, they lack dead cells and/or cellular debris they lack contaminants such as membrane contaminants, endoplasmic reticulum, Golgi apparatus, mitochondria or nuclear constituents, they bear at their membrane functional molecules of class I/II loaded with tumor antigenic peptides, they can stimulate the proliferation of specific T lymphocytes in vitro they can sensitize in vivo and in vitro dendritic cells which are then capable of activating the tumor-specific T cells, they possess the capacity when they are inoculated in vivo in particular intradermally, to cause established solid tumors to regress, they bear lymphocytic costimulatory molecules such as CD40 and CD80, and/or, they contain the ("heat-shock") protein HSP70, they lack the protein gp96, they contain interleukins or chemo-attractants or immunomodulators.

Another interesting characteristic of the texosomes is that they contain phosphatidylserine in the external layer. Phosphatidylserine (PS) is one of the major components of cell membranes, usually present very largely in the internal layer of the lipid bilayer. Under certain circumstances, such as the early steps of apoptosis, the PS is redistributed towards the external layer. The presence of PS in the external layer of the cytoplasmic membrane of the apoptotic cells constitutes a signal for recognition by the macrophages. In order to determine whether the PS is exposed at the surface of the texosomes, preparations of exosomes purified from supernatants of FON human melanoma cells were analyzed by the method described by Aupeix et al. (J. Clin. Invest. 99: 1546–1554, 1997). The phosphatidylserine content in the external layer of the FON samples (containing 390 microg/ml of proteins) is 460 nM of PS. The exosomes thus contain considerable quantities of PS in their external layer.

Assays making it possible to verify that the texosomes of the invention possess molecules usually present in the endosomes consist of electron microscopy and immunoblotting (Western blot). These assays make it possible to show that the texosomes of the invention express the transferrin receptor for transferrin, LAMP ("lysozyme associated membrane protein") molecules, molecules of class I/II, tumor antigens.

An assay making it possible to verify that the texosomes of the invention lack contaminants is electron microscopy and immuno-blotting with antibodies to calnexin which is present in the endoplasmic reticulum.

An assay making it possible to verify that the texosomes bear at their membrane functional molecules of class I/II loaded with tumor antigenic peptides consists of an antigenic presentation to T lymphocytes specific for the antigens of the tumor concerned (proliferation tests of T clones specific for antigens and restricted class I MHC).

It is also possible to use a test of secretion of cytokines (IFNγ, GM-CSF, TNFβ) by the above-mentioned T clones.

Figure 7:
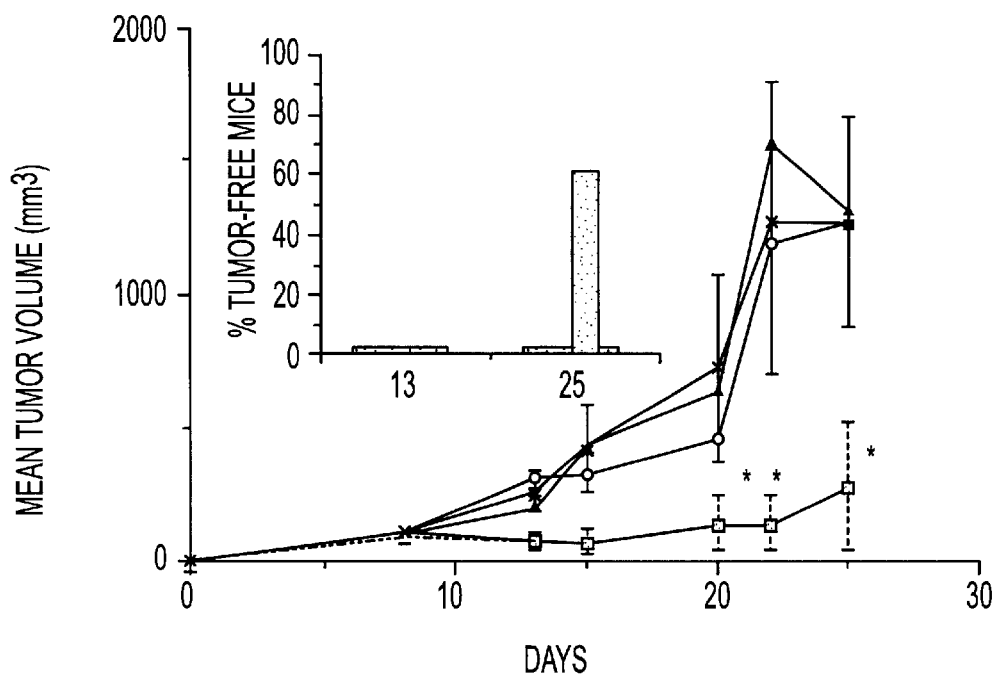

An assay making it possible to verify that there is in vivo and in vitro sensitization of the dendritic cells capable of activating tumor-specific T cells is given in FIG. 7 (proliferation and/or secretion test of cytokines by antigen-specific T clones by the "cross-priming" method: texosomes of a tumor MART-1+, HLA-A2-loaded one to a dendritic cell MART-1-, HLA-A2+).

An assay making it possible to verify that the texosomes possess the capacity when they are inoculated, in particular intradermally, to cause established solid tumors to regress is given in FIG. 6.

As an example, 10 to 40 µg of texosomes of tumor are injected intradermally on the same side as the tumor established 3 to 10 days previously; the animal bearing the tumor and the progressive disappearance of the tumor established 7 to 10 days previously are observed (in rodents, such as mice).

An advantageous texosome of the invention is constituted by a texosome such as that defined above and exhibiting on its surface class I and/or class II molecules of the MHC, optionally loaded with antigenic peptides and containing in its cytosolic fraction tumor antigenic molecules. More particularly, the preferred texosome also comprises one or more lymphocytic costimulatory molecules and/or the protein HSP70. In a particular embodiment, the texosome lacks the protein gp96.

According to an advantageous embodiment, the invention relates to a texosome such as that defined above, expressing on its surface class I and/or class II molecules of the major histocompatibility complex (MHC), and/or antigens characteristic of tumors and/or lymphocytic costimulatory/adhesion molecules and/or immunomodulators and/or chemo-attractants, exogenous with respect to the tumor cell from which the exosome is derived, or containing tumor antigens and/or immunomodulators and/or nucleic acids or cytotoxic agents or hormones exogenous with respect to the tumor cell from which the exosome is derived.

The invention also relates to a process for the preparation of texosomes such as those defined above. This process advantageously comprises a step in which a biological sample is provided and a step involving the isolation of texosomes from said sample.

The biological sample is advantageously constituted of membrane fractions, culture supernatants or lysates of tumor cells or even fresh tumor suspensions.

The biological sample may be tumor fragments obtained from operations after surgical excision (1st case) or even from organs bearing tumors (surgically excised organ) (2nd case) which are treated by mechanical dissociation (1st case) or by prolonged perfusion (2nd case).

The final cellular suspension is treated in the same manner as the culture supernatants.

The sample may also be cells treated by several successive cycles of freezing/thawing.

According to an advantageous embodiment, the biological sample used in the process of the invention is:

a blood sample taken from the efferent vein of the isolated tumor-bearing organ, or a plasma or serum sample of the circulating blood of a patient, or the drainage product (physiological serum possibly containing dexamethasone or a cytotoxic agent stimulating exocytosis of the texosomes) of an organ excised surgically and treated ex vivo by isolated perfused circuit for the drainage of the tumor it bears or also the supernatant of a tumor explant dissociated in vitro.

The efferent blood sample of the isolated tumor-bearing organ corresponds to 20 to 50 ml of blood taken from the principal efferent vein of the tumor-bearing organ, taken prior to surgical ablation.

The drainage product of an organ excised surgically and treated ex vivo by isolated-perfused circuit is obtained in the following manner.

In the case of an organ presenting an afferent artery and an efferent vein, the artery is characterized by a small plastic tube connected to an up-inclined pouch containing physiological serum with optionally other agents. The organ is drained and the liquid is returned by another small tube catheterizing the down- inclined vein (for example in the case of renal cancer or a cerebral glioblastoma).

The object of dexamethasone, optionally contained in the drainage product, is to increase the cellular stress and the exocytosis of the texosomes from the tumor cell.

The supernatant of a tumor explant dissociated in vitro is obtained in the following manner:

the mechanical dissociation of the tumor is performed leading to a unicellular suspension containing tumor cells and tumor stroma cells and cells of the immune system; this suspension may be irradiated and recovered for differential centrifugations.

As indicated above, in a particular embodiment of the invention the biological sample may be treated by one or more agents stimulating the production of texosomes. This treatment may comprise the addition of steroid agents (dexamethasone, for example), pharmacological agents (for example cytotoxic agents such as taxanes, cis-platinum, etc), agents likely to increase the quantity of multivesicular endosomes and/or irradiation of the sample.

As regards the irradiation, it must be sufficient to induce the cytostatic action of the tumor cells. The irradiation of the tumor cells may be done prior to placing them in culture or during or after placing the tumor cells in culture. Moreover, it is advisable to irradiate when the tumor cells are alive, i.e.:

either on the excised organ bearing the tumor prior to perfusion,
or on the cells in culture,
or on the mechanically dissociated cell suspension; but, in all cases, prior to tumor cell stress due to hypoxia/vascular necrosis/dehydration.

As regards the treatment with steroids, it enables cellular activation to be induced, leading to exocytosis of the texosomes.

As regards the treatment with pharmacological agents, it makes it possible:

to modify the cytoskeleton and rearrange the intracellular compartments in order to perturb the phenomena of internalization and exocytosis,
to depolymerize the microtubules.

As regards the treatment with an agent likely to increase the quantity of multivesicular endosomes, it is performed during the placing of the cells in culture; as agent mention may be made of nocodazole (drug leading to the depolymerization of the microtubules), bafilomycin (drug inhibiting the vacuolar ATPases) ("Bafilomycins: A class of inhibitors of membrane ATPases from microorganisms, animal cells and plant cells" (1988) Proc. Natl. Acad. Sci. USA 85: 7972–7976).

An advantageous process for the preparation of texosomes according to the invention is carried out:

a) either on cultures of tumor cells, and comprises:
   irradiation of the tumor cells before, during or after placing them in culture, at an intensity sufficient to induce the cytostatic action of the tumor cells and not exceeding 15,000 rads, and advantageously about 10,000 rads, or
   a treatment during culture of the tumor cells with steroids, for example dexamethasone or cytotoxic agents, for example 5-fluorouracil (5-FU) or cis-platinum, docetaxel, anthracyclin, a spindle poison, antipyrimidine or interleukin for example IL10, IL2, IL15, GM-CSF, or,
   a treatment with an agent capable of increasing the quantity of multivesicular endosomes, for example nocodazole (Gruenberg J et al., (1989) "Characterization of the Early Endosome and Putative Endocytic Carrier Vesicles in vivo and with an Assay of Vesicle Fusion in vitro" The Journal of Cell Biology 108: 1301–1316) and hence increase the production of texosomes, b) or on a sample of the physiological serum draining a surgically excised organ and treated ex vivo by isolated-perfused circuit for the draining of the tumor which it bears, or c) or on the supernatant of a tumor explant dissociated in vitro and comprising:
   a treatment with steroids, for example dexamethasone, or cytotoxic agents, for example 5-fluorouracil (5-FU); cis-platinum, taxanes or an interleukin for example IL-10, IL-2, GM-CSF.

The texosome isolation step may be performed according to different processes such as centrifugation, chromatography, electrophoresis, nanofiltration, etc. For example, it may involve a differential centrifugation of membrane fractions of culture supernatants or lysates of tumor cells or fresh tumor suspensions and recovery of the fraction(s) containing said exosomes (Raposo et al., J. Exp. Med. 1996, 183: 1161–1172). In this particular embodiment, the supernatant membrane fraction is that obtained after centrifugation at 100,000 g. It may advantageously involve a liquid phase electrophoresis which leads to the separation of biological materials according to their charge. The examples which follow show that this process may be advantageously used for the isolation of texosomes in good yields. This process is moreover particularly advantageous on an industrial scale.

The object of the invention is also a preparation process for texosomes such as defined above, comprising in addition:

either the genetic modification of the tumor cells by exogenous genes coding for class I and/or class II molecules of the major histocompatibility complex (MHC), and/or genes coding for antigens characteristic of tumors and/or genes coding for costimulatory/adhesion molecules or attractant chemokines, since it is possible to find the products of these exogenous genes expressed at the surface of the texosomes and/or be sequestered within the interior of the texosomes, or the in vitro modification of the texosomes produced by tumor cells, such as the introduction (by electroporation, by fusion with a synthetic liposome, by recombinant virus or by a chemical method) of proteins or nucleic acids or pharmaceutically defined medicines in and/or with the texosomes.

The invention also relates to texosomes capable of being obtained according to the process described above.

The texosomes of the tumor cells transfected as indicated above are recovered and used as tumor vaccines.

The texosomes modified in vitro as indicated above are designed to deliver the exogenous material to a target cell in vitro or in vivo.

As regards the fusion with a synthetic liposome, this process is performed for example as indicated in Nabel et al. (1996) or in Walker et al. (1997, Nature 387 pages 61 et seq.).

The invention also relates to antigen-presenting cells, in particular to B lymphocytes, macrophages, monocytes or dendritic cells, loaded with texosomes as defined above. Advantageously, they are dendritic cells.

The dendritic cells of the invention have, in particular, the following characteristics:

in tumor models which do not express class I molecules and which, consequently, do not have the capacity to stimulate CD8+ T cells, dendritic cells loaded with texosomes of tumor cells may present these tumor peptides to cytotoxic T cells in the context of the class I molecules of the MHC (characteristic No. 1)

dendritic cells loaded with texosomes of tumor cells injected intravenously or subcutaneously are also very efficacious (characteristic No. 2).

The following assay enables the characteristic No. 1 to be demonstrated.

In the human system, a class I-negative texosome, incubated in the presence of a class I-positive dendritic cell may lead to the stimulation of CD+8 T clones specific for the antigen contained in the texosome (see FIG. 7).

The following test enables the characteristic No.2 to be demonstrated.

In a mouse system in which the tumor is class I-negative and in which the texosomes themselves also lack class I molecules, these texosomes may, when they are incubated and loaded on to the dendritic cells, mediate an anti-tumor immune response whereas alone after intradermal injection they cannot.

The invention also relates to a preparation process for antigen-presenting cells such as defined above, comprising the steps of incubation of the antigen-presenting cells in the presence of texosomes such as defined above and recovery of above-mentioned antigen-presenting cells loaded with above-mentioned texosome.

The invention also relates to presenting cells loaded with texosomes and capable of being obtained by the process described above.

The object of the invention is also the use of texosomes such as those defined above for the sensitization of antigen-presenting cells, in particular B lymphocytes, macrophages, monocytes or dendritic cells or for the stimulation of specific T lymphocytes.

The invention also relates to a membrane vesicle freed from its natural environment, secreted by antigen-presenting cells loaded with texosomes such as defined above.

In order to obtain these membrane vesicles defined above, recourse may be had to a process comprising:

a step involving the preparation of a texosome such as that defined above, a step involving the incubation of a texosome with antigen-presenting cells, a step involving the differential centrifugation of membrane fractions of culture supernatants or lysates of the above-mentioned antigen-presenting cells, loaded with texosomes and a step involving the recovery of the fraction containing the above-mentioned membrane vesicles.

The object of the invention is also membrane vesicles such as defined above and capable of being obtained according to the process described above.

In this respect the invention relates to membrane vesicles produced by dendritic cells. Unexpectedly, the inventors have in fact demonstrated that the dendritic cells were capable of producing membrane vesicles having particularly advantageous immunogenic properties. Such vesicles have in particular been visualized, isolated and characterized from culture supernatants of dendritic cells, in particular immature human dendritic cells. Unlike vesicles described up to now, these vesicles are very advantageous to the extent that they present simultaneously and in considerable numbers molecules of classes I and II of the major histocompatibility complex. These membrane vesicles comprise a lipid bilayer surrounding a cytosolic fraction and are designated in what follows by the term "dexosome" on account of their origin and their unusual biological and biochemical properties. These vesicles indeed possess remarkable immunogenic properties because they are capable of stimulating the production and the activity of cytotoxic T lymphocytes both in vivo and in vitro, and because they enable the growth of established tumors to be suppressed in vivo, in a manner dependent on MHC-restricted T lymphocytes. The dexosomes hence constitute active principles particularly suited to non-cellular approaches to immunotherapy.

Special membrane vesicles in the sense of the invention are hence vesicles capable of being produced by dendritic cells, and which bear one or more class I molecules of the major histocompatibility complex and one or more class II molecules of the major histocompatibility complex.

The dexosomes advantageously bear lymphocytic costimulatory molecules, and in particular molecules CD63 and/or CD82 and/or CD86, and preferably at least CD86. The studies presented in the examples show in fact that the dexosomes are strongly labelled by antibodies directed specifically against these costimulatory molecules.

Moreover, the electron microscopical analyses show that the dexosomes are homogeneous and possess a diameter included between about 60 and 100 nm, most frequently between about 60 and 90 nm.

A particularly preferred variant of the invention is thus represented by a dexosome having a diameter included between about 60 and 90 nm, obtained from a dendritic cell, and comprising:

one or more class I molecules of the major histocompatibility complex, one or more class II molecules of the major histocompatibility complex, one or more CD63 molecules, one or more CD86 molecules; and one or more CD82 molecules.

In a particular embodiment of the invention, the dexosomes comprise in addition one or more antigenic peptides and/or are obtained from immature dendritic cells.

Still in accordance with a particular embodiment, the dexosomes lack H2-M markers, the li chain and calnexin (a specific marker of the endoplasmic reticulum).

Moreover, still in accordance with an advantageous embodiment, the dexosomes of the invention contain in addition phosphatidylserine (PS) in their external layer. Thus, exosome preparations purified from dendritic cell supernatants derived from bone marrow were analyzed by the method described by Aupeix et al. (J. Clin Invest. 99: 1546–1554, 1997). The phosphatidylserine content in the external layer of the BMDC samples (containing 35 microg/ml of proteins) is 80 nM of PS. The dexosomes thus contain considerable quantities of PS in their external layer.

The dexosomes can be prepared according to a methodology comprising a first step for obtaining dendritic cells or a cell culture containing dendritic cells, an optional second step during which the cells may be sensitized to antigens of interest, and a third step comprising the production of dexosomes from these cell cultures. These different steps may be advantageously carried out according to the methodologies described hereafter.

Preparation of Dendritic Cells

The first step of the process comprises the the provision of (a) culture(s) of dendritic cells. They may be cultures of cells enriched in dendritic cells, even cell cultures consisting essentially of dendritic cells. Advantageously, they are obviously human dendritic cells.

The preparation of dendritic cells has been well documented in the literature. Thus, it is known that these cells can be obtained from stem cells of the immune system or from monocyte precursors or even isolated directly in a differentiated form (review by Hart, Blood 90 (1997) 3245).

The production of dendritic cells from stem cells is illustrated for example by Inaba et al. (J. Exp; Med. 176 (1992) 1693), Caux et al. (Nature 360 (1992) 258) or Bernhard et al. (Cancer Res. 55 (1995) 1099). These publications show in particular that dendritic cells can be produced by culture of bone marrow in the presence of granulocyte-macrophage—colony stimulation factor (GM-CSF) or, more exactly, from hematopoietic stem cells (CD34+) by culture in the presence of a combination of cytokines (GM-CSF+TNFα).

The production of dendritic cells from monocyte precursors is illustrated for example by Romani et al. (J. Exp. Med. 180 (1994) 83), Sallusto et al. (J. Exp. Med. 179 (1994) 1109), Inaba et al. (J. Exp. Med. 175 (1992) 1157) or also Jansen et al. (J. Exp. Med. 170 (1989) 577). These methodologies are based essentially on the collection of mononucleated cells in blood and placing them in culture in the presence of various combinations of cytokines. A specific method consists of treating the monocyte precursors of the blood in the presence of combinations of cytokines such as interleukin4+GM-CSF or interleukin-13+GM-CSF for example. This process is also illustrated by Mayordomo et al., 1995. Moreover, it is also possible to treat the monocyte precursors with pharmacological agents for cellular differentiation, such as calcium channel activators.

Another approach to the production of dendritic cells consists of isolating differentiated dendritic cells from biological samples. This approach has been described for example by Hsu et al. (Nature Medicine 2 (1996) 52). The methodology described by that group consists essentially of harvesting peripheral blood samples and of subjecting them to different gradients and centrifugations so as to extract the dendritic cells from them.

The preferred methodology in the framework of the present invention is based on the production of dendritic cells from monocyte precursors or from bone marrow. These methodologies are illustrated in the examples. More particularly, preference is given to the use in the framework of the present invention of dendritic cells obtained by treatment of monocyte precursors (contained in the blood or bone marrow) in the presence of a combination of GM-CSF+IL-4 or GM-CSF+IL-13.

Moreover, for the implementation of the present invention, it is quite especially advantageous to use a population of dendritic cells comprising immature dendritic cells. Advantageously, a population of dendritic cells composed mainly (i.e. to at least 60%, preferably 70%) of immature dendritic cells is used. The immature state of the dendritic cells corresponds to an early stage of their development, at which they exhibit a high endocytic activity and express low levels of classes I and II molecules of the MHC and lymphocytic costimulatory molecules at their surface. Surprisingly, the inventors have indeed found that only immature dendritic cells were capable of producing membrane vesicles in significant quantity. This discovery is all the more surprising as the dendritic cells at the immature stages are known for their low capacity to stimulate the T lymphocytes and hence for their low biological activity (Cella, Nature London, 388 (1997) 782).

The first step of the process of the invention may thus advantageously comprise the preparation of a population of dendritic cells comprising immature dendritic cells, in particular starting from monocyte precursors, more particularly by treatment with a combination of cytokines such as GM-CSF+IL-4 or GM-CSF+IL-13.

Moreover, it is also possible to use in the framework of the present invention immortalized populations of dendritic cells. They may be immortalized lines of dendritic cells (line D1 used in the examples or any other line produced by example by introduction of the myconcogene into the dendritic cells). They may also be dendritic cells prepared and then immortalized in vitro. The value of immortalized dendritic cells resides in the constitution of libraries of cells sensitized to given groups of antigens, which can be used industrially to prepare dexosomes capable of being administered to whole families of patients.

Once the dendritic cells are prepared they may be maintained in culture, purified further, stored or used directly in the following steps of the process.

Sensitization of the Dendritic Cells

The dexosomes of the invention can be prepared from dendritic cells not loaded with antigens, i.e. not bearing specific antigens in their membranes or their cytosol. Such dexosomes are then designated as being "naive" or "virgin".

According to a preferred embodiment, the dexosomes of the invention are however prepared from dendritic cells sensitized to an antigen or to a group of antigens. In this embodiment, the dexosomes carry themselves said antigen (s) and are thus capable of inducing a response to them.

Different processs may be used to sensitize the dendritic cells to antigens. These processs have been mentioned above and comprise in particular:

the placing of the dendritic cells in contact with antigenic peptides ("peptide pulsing"). This approach consists of incubating the dendritic cells for a variable time (usually from about 30 minutes to about 5 hours) with one or more antigenic peptides, i.e. with a peptide derived from an antigen, such as might result from the treatment of said antigen with an antigen-presenting cell. This type of approach has been described for example for antigenic peptides of the HIV virus, influenza virus or HPV or for peptides derived from the antigens Mut1, Mart, Her2 or Neu for example (Macatonia et al., J. Exp. Med. 169 (1989) 1255; Takahashi et al., Int. Immunol. 5 (1993) 849; Porgador and Gilboa, J. Exp. Med. 182 (1995) 255; Ossevoort et al., J. Immunother. 18 (1995) 86; Mayordomo et al., previously mentioned; Mehta-Damani et al., J. Immunol (1994) 996). It is also possible to incubate the dendritic cells with an acidic peptide eluate of a tumor cell according to the methodology described by Zitvogel et al. (1996, previously mentioned).

the placing of the dendritic cells in contact with one or more antigens ("antigen pulsing"). This approach consists of incubating the dendritic cells not with one or more antigenic peptides but with the intact antigen(s). The value of this process resides in the fact that the antigen will be converted into antigenic peptides by the natural mechanisms of the dendritic cell, so that the resulting antigenic peptides presented by the dendritic cell ought to provide a better immunogenicity. This approach has been illustrated for example by Inaba et al. (J. Exp. Med. 172 (1990) 631) or by Hsu et al. (Nature Medicine 2 (1996) 52).

- the placing of the dendritic cells in contact with one or more antigenic protein complexes. This approach is similar to the preceding one but may increase the efficacy of processing and/or presentation of the antigen. In particular, the antigen may be used in a soluble form or complexed with targetting elements which enable, in particular, membrane receptors like the mannose receptors or the immunoglobulin receptors (Rfc) to be targetted. It is also possible to make the antigen particulate so as to improve its penetration or even its phagocytosis by the cells.
- the placing of the dendritic cells in contact with cells or membranes of cells expressing antigens or antigenic peptides. This process is based on the direct transfer of antigens or antigenic peptides by fusion of cells or cell membranes. This approach has been illustrated for example by the fusion between dendritic cells and membranes of tumor cells (Zou et al., Cancer Immunol. Immunother. 15 (1992) 1).
- the placing of the dendritic cells in contact with membrane vesicles containing antigens or antigenic peptides (in particular exosomes from tumor cells such as already described above). This approach to sensitization of the dendritic cells using exosomes such as demonstrated in the present invention, is particularly advantageous in as much as it does not require knowledge of particular antigens and in as much as the antigen peptides loaded are in a native conformation. This technology is illustrated in the examples.
- the placing of the dendritic cells in contact with liposomes containing antigens or antigenic peptides (Nair et al., J. Exp. Med. 175 (1992) 609).
- the placing of the dendritic cells in contact with RNAs coding for antigens or antigenic peptides (see Boczkowsky et al., 1996, previously mentioned).
- the placing of the dendritic cells in contact with DNAs coding for antigens or antigenic peptides (possibly incorporated in vectors of the plasmid, viral or chemical type). Thus, one method of sensitizing the dendritic cells consists for example of infecting the dendritic cells with a virus against which protection is desired. This has been described for example for the influenza virus (Bhardwaj et al., J. Clin. Invest. 94 (1994) 797; Macatonia et al., previously mentioned). Another approach consists of delivering, by means of a virus or other nucleic acid transfer vectors, a DNA coding for the antigen(s) or antigenic peptides of interest. Such an approach has been illustrated for example by Arthur et al. (Cancer Gene Therapy, 1995) or by Alijagie et al. (Eur. J. Immunol. 25 (1995) 3100). Some viruses such as the adenoviruses, the AAV or the retroviruses seem capable of being used for this purpose to deliver a nucleic acid into a dendritic cell.

Preferred processes in the framework of the present invention are the sensitization methods using membrane vesicles (of the exosome type), antigenic peptides, vectors, RNAs or acidic peptide eluates of tumors (APE). The use of membrane vesicles as well as "peptide pulsing" and the APE method are illustrated in the examples and are quite particularly preferred.

Production of the Dexosomes

When the populations of dendritic cells have been obtained and optionally sensitized to one or more antigens, the dexosomes can be prepared.

This preparation comprises an optional first step of treatment of the cells, followed by a second step of isolation of the dexosomes.

The first treatment step of the cells results from the demonstration by the inventors that the production of dexosomes by the dendritic cells is a regulated phenomenon. Thus, in the absence of treatment, the quantites of dexosomes produced are relatively low. In particular, when a population of mature dendritic cells not stimulated beforehand is used, the production of dexosomes is practically undetectable. The inventors have thus shown that the production of dexosomes was essentially dependent on the type of dendritic cells and the implementation of a treatment of these cells. These preliminary elements are what make it possible to obtain dexosomes having useful properties in quantities significant for industrial use. A treatment of the dendritic cells is thus advantageously performed so as to stimulate the production of dexosomes by these cells. This stimulating treatment may be performed either by the culture of the cells in the presence of certain cytokines, or by irradiation of the cells, or by lowering the pH of the culture, or by combining these different types of treatment.

In the first embodiment the dendritic cells are incubated in the presence of a cytokine selected preferably from gamma interferon (IFN$\gamma$), interleukin-10 (IL-10) and interleukin-12 (IL-12), and preferably gamma interferon and IL-10. As illustrated in the examples, these cytokines seem to exert a quite pronounced stimulating effect on the production of dexosomes (factor 3 to 5). Furthermore, surprisingly, no stimulating effect was observed in the presence of the following cytokines: IL-1$\beta$, IL-2, IL-4, IL-6 and IL-15, and an inhibitory effect has even been observed in the presence of lipopolysaccharide (LPS) or TNF$\alpha$, which are however described as stimulating the maturation of the dendritic cells. Hence these results show (i) the regulated character of the production of dexosomes and (ii) the specific effect of certain cytokines on this production. In addition, these results illustrate the surprising value of using immature dendritic cells, and the use, in the stimulation step, of cytokines inducing an immature state of the cells, such as IL-10 in particular. In this embodiment, the cytokines are used at doses adjustable by the specialist skilled in the art as a function of (i) the cytokine, (ii) the cell population and (iii) possible performance of other treatments. It is understood that the cytokines are preferably used at subtoxic doses. The doses of interleukin are usually comprised between 1 and 100 ng/ml, and preferably between 1 and 50 ng/ml. The interferon may be used at doses comprised between 1 and 500 IU/mil, and preferably between 5 and 200 IU/ml.

In the second embodiment, the dendritic cells are subjected to irradiation. The results presented in the examples indeed show that irradiation of the cells also makes it possible to increase the production levels of dexosomes. Irradiation is usually performed at between 1000 and 5000 rads, and preferably between 2000 and 4000 rads, and most favourably at approximately 3000 rads.

The second step consists of the isolation of the dexosomes. The objective of this step is to separate the dexosomes from the dendritic cells and/or the culture medium. This step makes it possible in particular to obtain a composition enriched in dexosomes and essentially free of intact cells. Preferably, this step leads to a composition comprising at least 70% and preferably at least 85% of dexosomes.

The isolation of the dexosomes may be carried out according to different separation procedures for biological materials. As described previously for the texosomes of tumor cells, these processes may be based on the differences of size, mass, charge or density of the dexosomes.

Thus, the dexosomes may be isolated by centrifugation of the culture medium or the culture supernatant or membrane fractions or lysates of dendritic cells. The isolation may be done for example by a differential centrifugation and/or density gradient cenntrifugation, followed by recovery of the fraction(s) containing said dexosomes. This type of methodology is based on the separation, by means of successive centrifugations, of the membrane vesicles on the one hand and cells, cellular debris, internal vesicles, etc., on the other. In this particular embodiment, the fraction containing the dexosomes is usually that obtained after ultracentrifugation at 100,000 g. This method is illustrated in particular in Examples 1 and 8.

The isolation step of the dexosomes may also be performed by chromatography, electrophoresis and/or nanofiltration.

A liquid phase and/or density gradient electrophoresis may be advantageously performed. The liquid phase electrophoresis, which leads to the separation of biological materials according to their charge, is quite advantageous. Example 11 below indeed shows this procedure may be profitably used for the isolation of exsomes in good yields. This procedure is, moreover, particularly advantageous on an industrial scale.

Purification may also be performed by chromatography. Mention may be made in particular of ion exchange chromatography, gel permeation (or exclusion) chromatogrphy or hydrophobic chromatography. In view of the lipid nature of the dexosomes, ion exchange chromatography is particularly useful. Nanofiltration may be performed according to known procedures on cell supernatants.

Recourse to chromatographic and/or electrophoretic procedures and/or nanofiltration constitutes another important feature of the present invention since it allows, compared to current technologies, the production of improved quality in quantities suitable for industrial use (in particular pharmacological).

In this respect, the invention also relates to a method of preparation of membrane vesicles comprising at least a separation step by electrophoresis, chromatography or nanofiltration. This process is more particularly suited to the preparation of membrane vesicles of the exosome type, such as texosomes or dexosomes. In this process, the separation step by electrophoresis or chromatography may be performed directly on a culture supernatant, a cell lysate or a pre-purified preparation. The electrophoresis is more preferably a liquid phase electrophoresis.

The dexosomes exhibit remarkable properties which are illustrated in the examples. Thus, the dexosomes stimulate the proliferation of cytotoxic T lymphocytes in vitro. Furthermore, the dexosomes are capable of blocking tumor growth in vivo. These vesicles are thus capable of presenting antigens of interest very efficiently in combination with class I and class II molecules of the MHC. The dexosomes hence have very many uses in the fields of cancer and parasitic or infectious diseases, for example. In addition, at high doses (likely to induce tolerance), the dexosomes may also be used in the treatment of diseases such as allergy, asthma or autoimmune diseases. In addition, the "naive" dexosomes may also be used as adjuvant to stimulate and/or modulate an immune response.

The object of the invention is also the use:
of texosomes such as defined above, or
antigen-presenting cells such as defined above, or
dexosomes such as defined above,
    for the stimulation and, optionally, the amplification in vitro of T lymphocytes specific for antigens contained in above-mentioned texosomes, antigen-presenting cells or dexosomes—or of B lymphocytes, and in particular for the stimulation and amplification in vitro of T lymphocytes.

The invention also relates to the use of texosomes such as defined above, or of antigen-presenting cells such as defined above or of dexosomes such as defined above for the ex vivo selection of a repertoire of T lymphocytes capable of recognizing specific antigens contained in above-mentioned texosomes, antigen-presenting cells or dexosomes.

The object of the invention is also a medicine containing as active substance at least one texosome such as defined above, one antigen-presenting cell such as defined above and/or a dexosome such as defined above, in combination with a pharmaceutically acceptable vehicle.

Advantageously, the invention relates to a medicine such as defined above for use in the treatment of cancers, parasitic or infectious diseases.

More preferably, the medicine contains texosomes or dexosomes such as defined above.

According to another embodiment, the invention relates to a medicine such as defined above for use in the treatment of the diseases of the allergy or asthma type or autoimmune disease.

As appropriate formulation, the texosomes or dexosomes may be contained in physiological serum in an ampoule or any other appropriate means (syringe, pouch, etc). They may be prepared immediately prior to use or stored, for example frozen at −80° C. The solutions used may be composed of saline solutions, optionally supplemented with stabilizing agents and/or adjuvants. The stabilizing agents may be in particular proteins or molecules of high molecular weight. Mention may be made more particularly of proteins such as human serum albumin or molecules such as dextran or poloxamer, for example.

The compositions of the invention may also contain or be used in combination with one or more adjuvants. The adjuvant may be more particularly any immunostimulating pharmacological agent such as for example a cytokine (in particular interleukin-12). Such agents are classically used in the clinical protocols or in vaccinating compositions. Moreover, the adjuvant according to the invention may also be an agent capable of stimulating the production of dendritic cells in vivo. As an example, mention may be made of compound Flt3. The combined use of this type of agent makes it possible to increase the number of dendritic cells and thus to improve potentially the efficacy of the compositions of the invention.

Another object of the invention thus relates to a combination of texosomes and/or dexosomes and an adjuvant for the purpose of simultaneous use, separate use or use of each at intervals.

An appropriate mode of administration of the medicines of the invention consists of injections, and in particular intradermal or subcutaneous injections. This mode of administration is particularly suitable when the active substance of the medicine is constituted of dendritic cells loaded with texosomes or dexosomes.

The appropriate dosages are 0.01 to 10, and in particular 0.10 to 5 and even more particularly 0.15 to 2 µg/kg of body weight, and 10 µg for the intradermal reaction tests.

The medicines of the invention may also be used at 100 µg for prophylactic vaccination treatments.

The objectives designed to be attained by the use of the medicines of the invention are:
    delayed hypersensitivity (tests in cancer patients), or
    prophylactic therapy, or use in the framework of the detection of the frequency of specific cytotoxic lymphocytic precursors or secretors of interferon by the limiting dilution process.

The objective is to use the autologous or allogeneic dendritic cells preincubated with the texosomes of the invention as targets of peripheral lymphocytes of subjects bearing tumors before, during and after anti-tumor treatment (standard treatment or specific active immunization).

The invention also relates to the use of a texosome such as defined above or antigen-presenting cell such as defined above or of a dexosome such as defined above for the preparation of a medicine designed for the treatment of tumors, in particular solid, ascitiic and hematopoietic tumors.

As solid tumors, mention may be made of: cancer of the kidney, breast, colon, lung, stomach, liver, melanomas, sarcomas, etc . . .

As hematopoietic tumors, mention may be made of: leukemias, Hodgkin and non-Hodgkin malignant lymphomas.

As indicated previously, the compositions of the invention, in particular the compositions containing dexosomes, can also be used for the treatment of parasitic or infectious diseases. For this type of use, the dexosomes are loaded with antigens or peptides of the parasite or the infectious agent (virus).

The invention also relates to the use of a texosome such as defined above or of a dexosome as defined above in the framework of a delayed hypersensitivity test of the cancer or also as diagnostic tool to investigate the frequency of specific cytotoxic CTL precursors.

The invention also relates to the use of a texosome or a fraction or a constitutive constituent of a texosome such as defined above or of a dexosome such as defined above for the transfer of biological material into a cell in vitro or in vivo.

The invention also relates to the creation of texosome libraries derived from tumor cells of a common or different histological type.

These latter are composed of mixtures of texosomes made from tumor cell lines for a given type of cancer. These texosome libraries may enable antigen-presenting cells, in particular dendritic cells, to be sensitized against all the tumors of this type.

The invention also relates to mixtures of texosomes or dexosomes.

For example, mention may be made of mixtures of texosomes for genetically related tumors (cancer of the breast and ovary) or exhibiting known mutations p53, p16 (breast cancer, sarcoma).

Mention may also be made of mixtures of tumor texosomes with vesicles derived from immortalized cells and transfected to express co-stimulatory molecules, adhesion molecules, attractant chemokines (different from those expressed on the texosomes).

The present invention will be described in more detail with the aid of the examples which follow, which must be considered as illustrative and not limiting.

LEGENDS TO FIGURES

Table 1. The tumor cell lines were incubated for 24 h to a density of one million cells per milliliter. The texosomes were then prepared (see Example) from culture media by differential ultracentrifugation. The texosomal protein concentration is measured by the Bradford test (BioRad Protein Assay {BioRad}).

MZ-2 is described in Traversari et al., (1992)

The * signify that the different primary lines were established and characterized in the clinical biological laboratory of the Gustave Roussy Institute and are available on request.

FIGS. 1A and B. Morphology of the multi-vesicular endosomes and of the texosomes derived from TS/A cells.

A. Ultrathin sections of the TS/A cells analyzed by electron microscopy. Detail of the cytoplasm showing an endosomal compartment containing vesicles 60–80 nm in diameter.

B. Preparation of texosomes from TS/A cells analyzed in electron microscopy by the procedure on the intact vesicle (Raposo et al., (1996)). The preparations of texosomes contain a major population of vesicles 60–80 nm in diameter, of a size and morphology similar to the internal vesicles of the multivesicular endosomes shown in A.

Figure 2A:
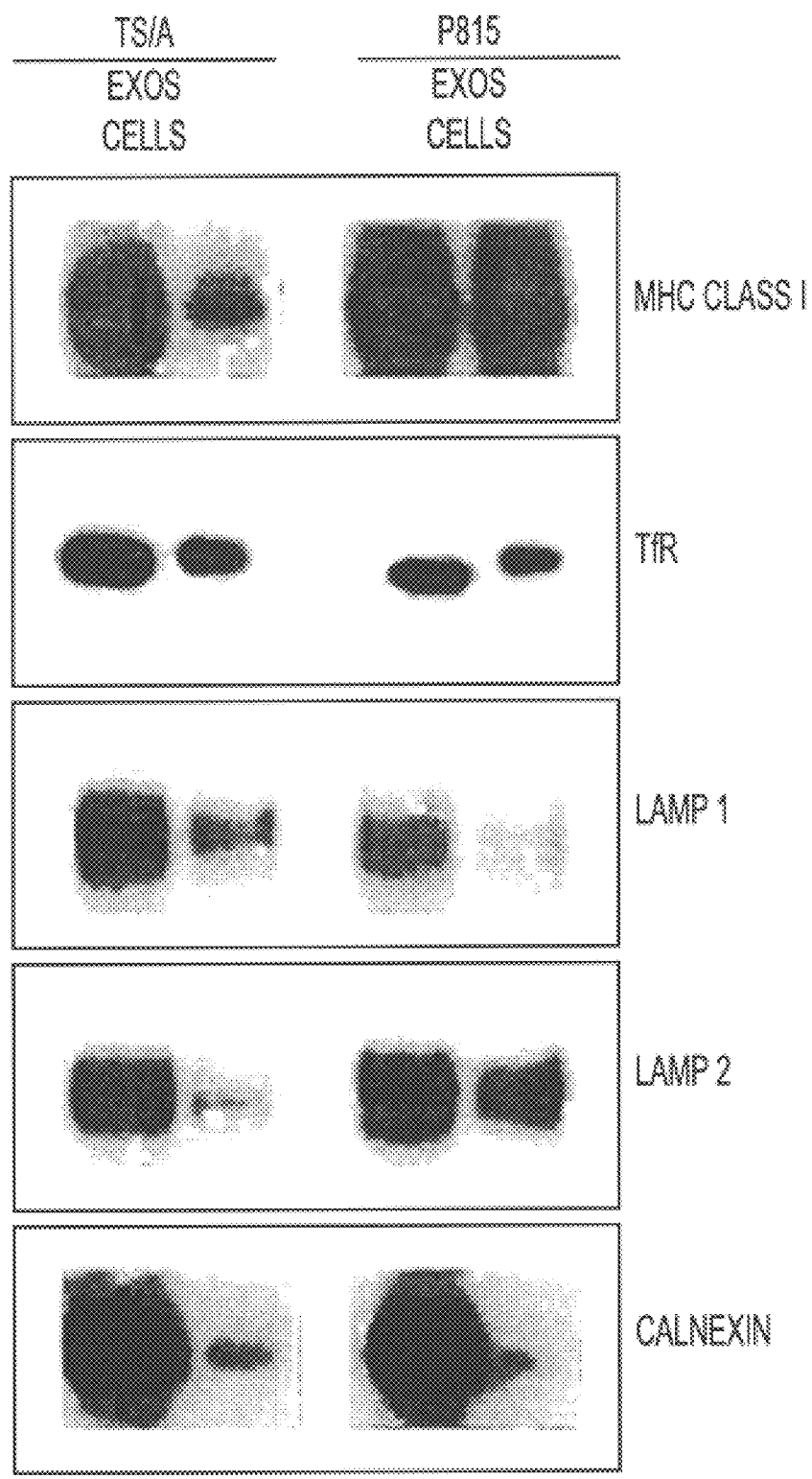
Figure 2B:
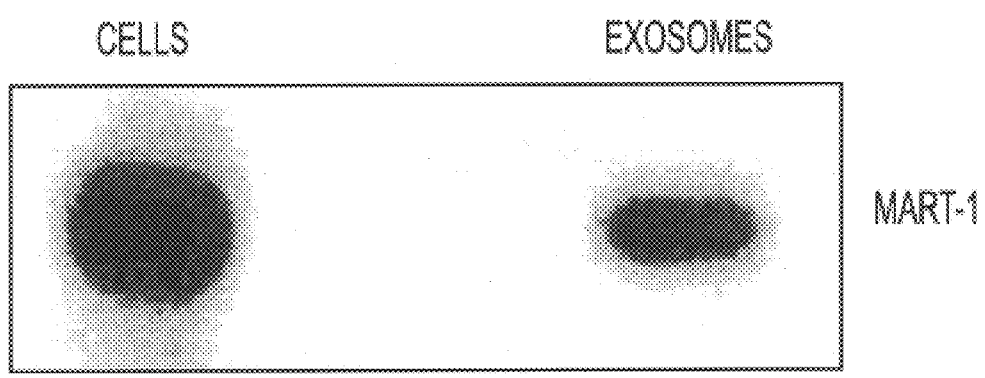
Figure 2C:
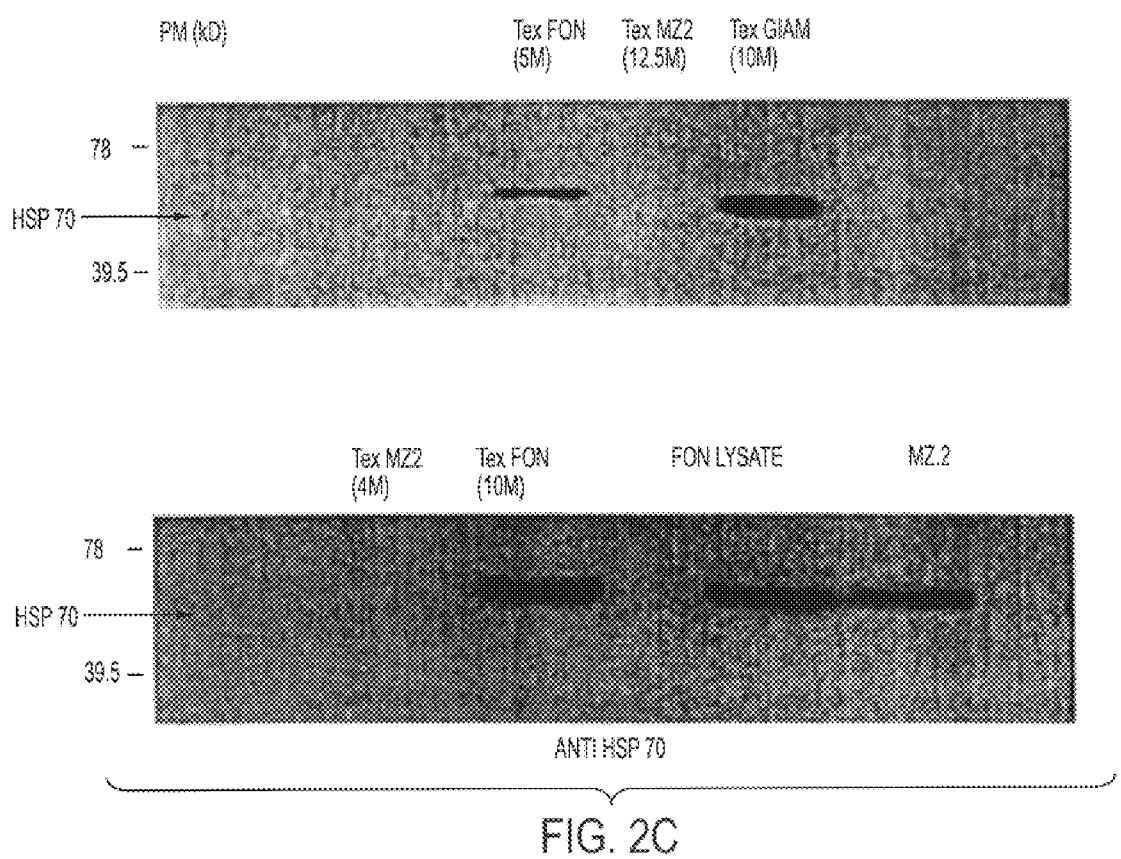
Figure 2D:
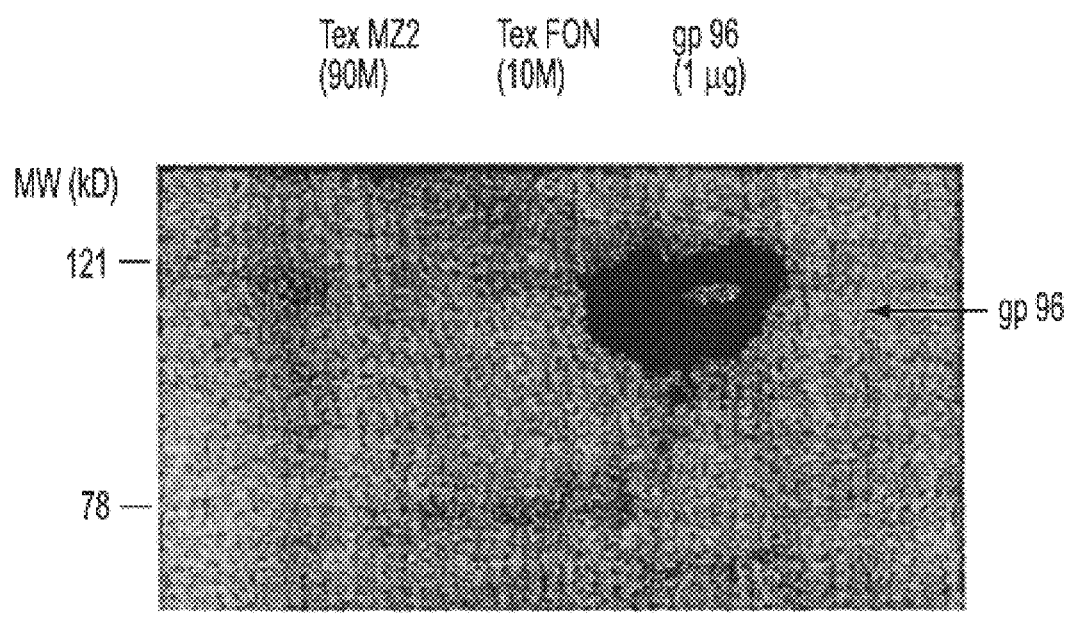

FIGS. 2A, B, C, and D. Presence of different markers in the texosomes of tumor cells.

A. Two micrograms of texosomal proteins (Exos) or $2 \times 10^5$ tumor cells were analyzed by Western blot with the aid of monoclonal antibodies specific for: class I molecules of the MHC (Machold Robert P. et al. (1995) "Peptide Influences the Folding and Intracellular Transport of Free Major Histocompatibility Complex Class I Heavy Chains" J. Exp. Med. 181: 1111–1122), the transferrin receptor (TfR) (corresponding antibody being H68.4 described in Biochimica et Biophysica Acta (1992) 1136 (1): 28–34), Lamp 1 and 2 (rat anti-mouse monoclonal antibodies, Pharmingen) and calnexin (Hebert Daniel N. et al. (1995) "Glucose Trimming and Reglucosylation determine Glycoprotein Association with Calnexin in the Endoplasmic Reticulum" Cell 81: 425–433).

B. Ten micrograms of texosomal proteins of a melanoma cell line (FON) or 10 µg of total proteins from the same cells were analyzed by Western blot with the aid of an anti-MART-1 antibody (Marincola F. et al., (1996) "Analysis of expression of the melanoma associated antigens MART-1 and gp100 in metastatic melanoma cell lines and in "in situ" lesions, Journal of Immunotherapy 19: 192–205).

C. The texosomal proteins of a melanoma cell line (FON) or total proteins of the same cells were analyzed by Western blot with the aid of an anti-HSP70 antibody.

D. The texosomal proteins of a melanoma cell line (FON) or of the MZ-2 line were analyzed by Western blot with the aid of an anti-gp96 antibody.

Figure 3:
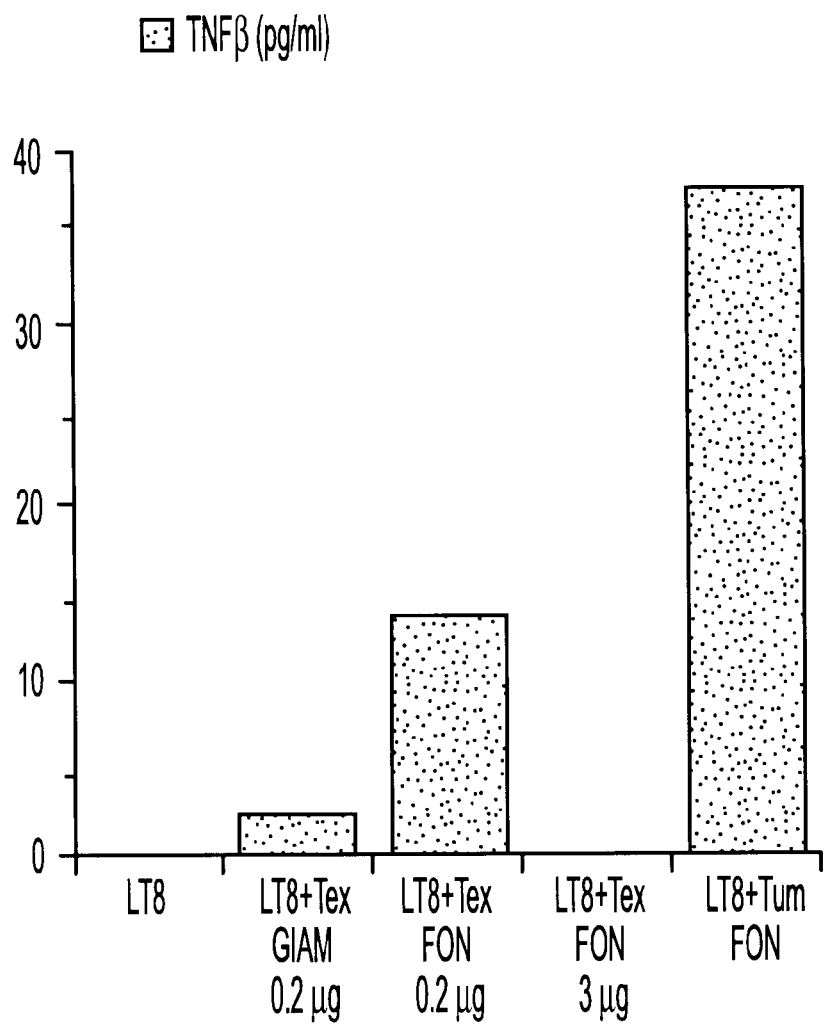

FIG. 3. The texosomes derived from a MART-1-positive tumor line (FON) stimulate a T clone specific for MART-1.

Twenty thousand cells of the T clone LT8 (or LT12, results not shown) were incubated with texosomes derived from FON (cell lines MART-1 and HLA-A2 positive) or GIAM (cells of a nephroma line, MART-1 negative) as negative control for 48 h. The production of TNFβ by the cells of the T done was measured by biological assay with the WEHI cells (Espavik et al.). The texosomes induce the production of IFN by the T clone, thus revealing the presence of HLA-A2/peptide complexes derived from MART-1 at the surface of the texosomes.

"LT8+TexGIAM" corresponds to LT8 T clones incubated in the presence of texosomes derived from GIAM tumor cells;

"LT8+TexFON" corresponds to LT8 T clones incubated in the presence of texosomes derived from FON tumor cells;

"LT8+TumFON" corresponds to LT8 T clones incubated in the presence of texosomes derived from GIAM tumor cells;

The conditioned cells are shown along the abscissa and the quantity of TNFβ (pg/ml) produced along the ordinate.

Figure 4:
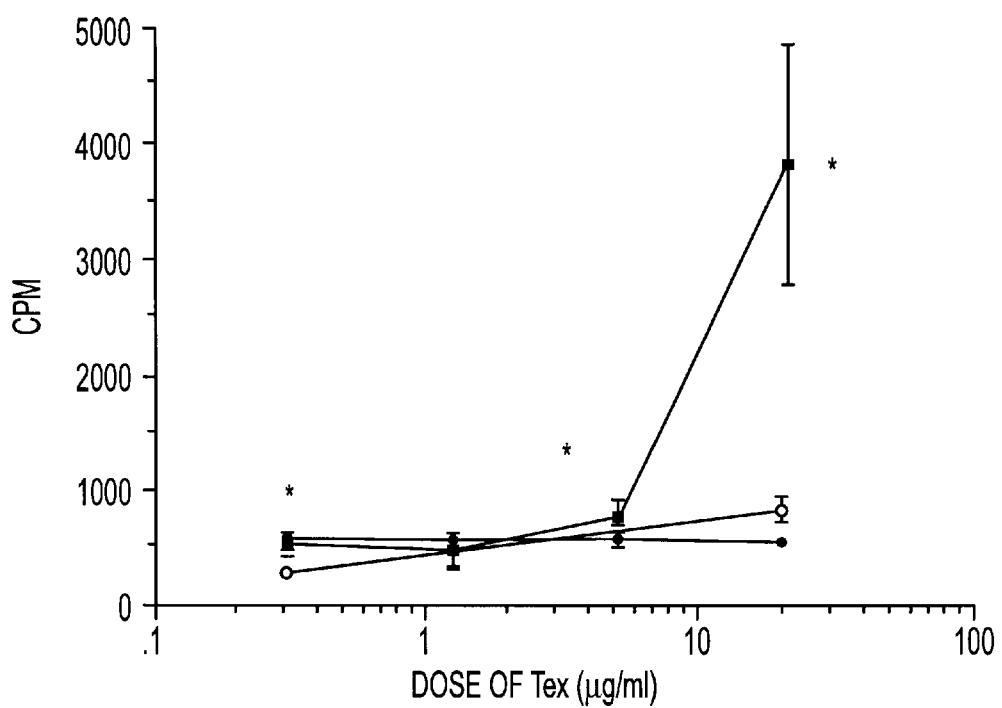

FIG. 4. The texosomes from P815 cells expressing βGal stimulate splenocytes of mice immunized by recombinant βGal adenoviruses.

Splenocytes ($10^5$) of BALB/c mice, immunized 2 months previously with $10^6$ pfu of recombinant βGal adenovirus and which had rejected a tumor expressing βGal, were incubated with texosomes derived from P815 cells (unfilled diamonds ◇) or P815-βGal cells (filled squares ■). Splenocytes not incubated with texosomes give the background symbolized by filled circles (●). After 5 days of culture, 1 μCi of tritiated thymidine was added per culture well. The incorporation of tritium into the cellular DNA was measured 18 h later. The significantly different results according to the exact method of Fisher are marked *.

The quantity of texosomes derived from the P815 tumor cells (μg/ml) is shown along the abscissa and the counts per minute (CPM) along the ordinate.

Figure 5:
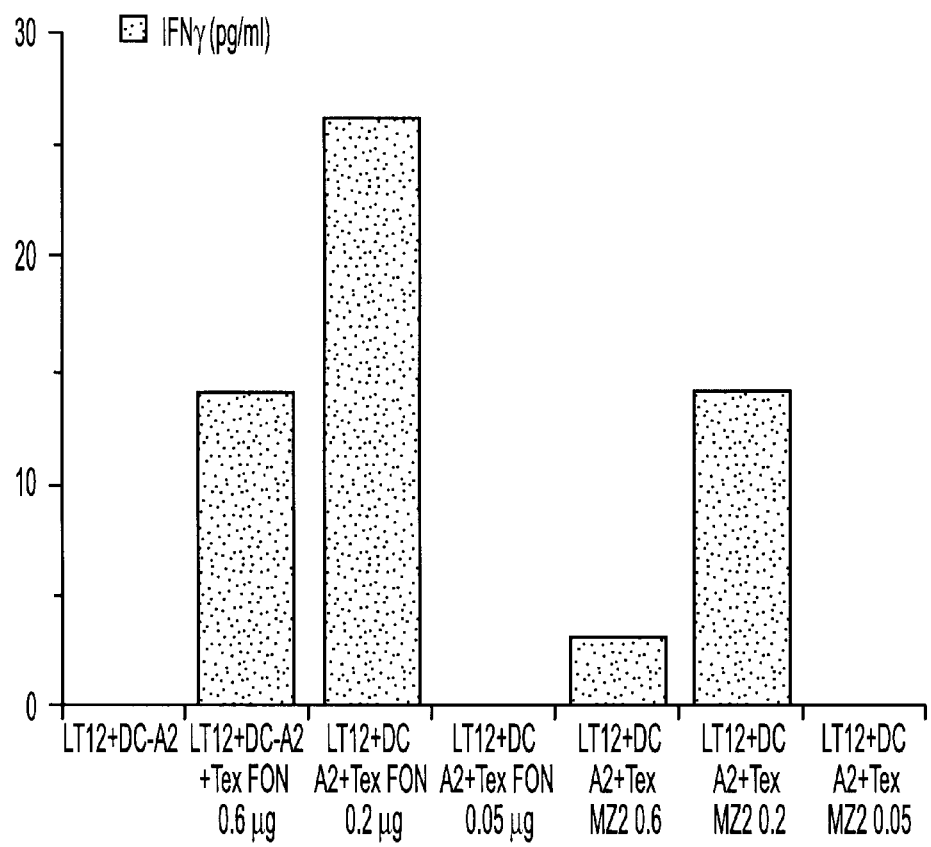

FIG. 5. The tumor antigen MART-1 contained in texosomes may be presented to T lymphocytes by dendritic cells.

Increasing doses of texosomes derived from the tumor cell lines FON (MART-1+, HLA-A2+, A1−) and MZ2 (MART-1+, HLA-A2−, A1+) were incubated with the LT12 T clones (20,000 cells per well of a 96 well microtiter plate) (specific for the HLA-A2/peptide of MART-1) in the presence of HLA-A2+dendritic cells derived from circulating macrophages (DCA2) (Sallusto, F. and Lanzavecchia A., 1994, Efficient presentation of soluble antigen by cultured human dendritic cells is maintained by GM-CSF and IL-4 and down-regulated by TNFα J. Exp. Med. 179: 1109–1118). The IFNγ secretion shown along the ordinate (pg/ml) was measured in the culture supernatants after 2 days. The texosomes derived from FON as well as those derived from MZ2 induced IFN secretion by LT12 and LT8 (results not shown). The FON cells also induced strong IFNγ secretion by the T clones, whereas the MZ2 cells, which do not express an adequate haplotype of the HLA molecule (HLA-A2), did not induce IFNγ production.

Figure 6A:
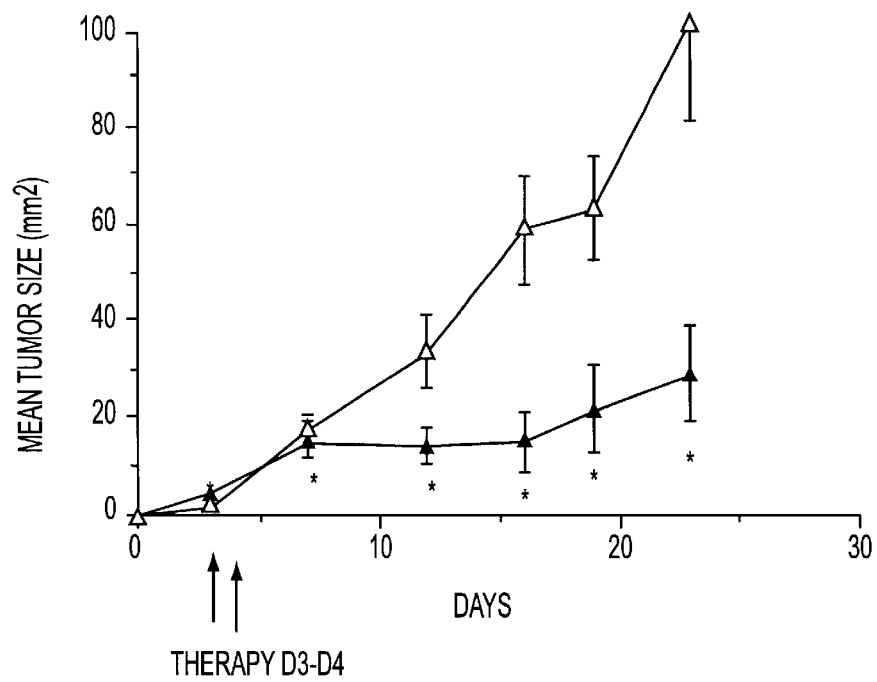
Figure 6B:
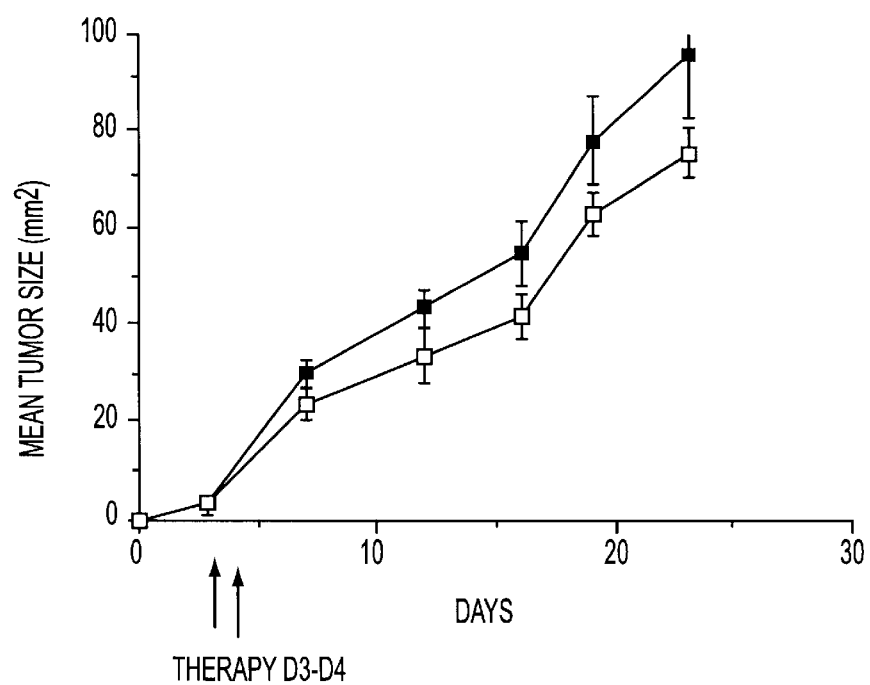

"LT12+DCA2" corresponds to LT12 T clones incubated in the presence of HLA-A2+ dendritic cells;

"LT12+DCA2+TexFON" corresponds to LT12 T clones incubated in the presence of dendritic cells loaded with texosomes derived from FON tumor cells;

"LT12+DCA2+TexMZ2" corresponds to LT12 T clones incubated in the presence of dendritic cells loaded with texosomes derived from MZ2 tumor cells;

FIGS. 6A and 6B. Anti-tumor effects of the texosomes in vivo.

One hundred thousand TS/A tumor cells were injected into BALB/c (A) or Nude (B). Three days later each mouse received two successive injections at a 24 h interval (shown as D3 and D4 on the Figure) of 20 μg to 30 μg of texosomes intradermally. The size of the tumors was then measured twice a week. The statistical analyses were made by the exact method of Fisher (95% significance is indicated by *).

A. Two groups of 5 mice received texosomes derived from TS/A (filled triangles) or MCA38 (unfilled triangles) (a colon adenocarcinoma cell line derived from a C57BL/6 mouse) as negative control. Only the texosomes derived from TS/A have an anti-tumor effect in vivo.

B. Two groups of Nude mice received the same doses of the same texosome preparations in parallel (■: TS/A exosomes; □ MC38 exosomes).

No anti-tumor effect was observed on the Nude mice. The T lymphocytes are thus necessary for the anti-tumor effects of texosomes in vivo.

Time in days is indicated along the abscissa and the mean size of the tumor ($mm^2$) along the ordinate.

FIG. 7. Dendritic cells derived from bone marrow sensitized by the texosomes derived from tumor cells induce the total eradication in vivo of established solid tumors.

Five hundred thousand P815 tumor cells were injected into the right flank of DBA/2 mice 10 days before the treatment. The treatment consisted of a single injection of texosomes (10 μg/mouse) in the same flank but at a distance from the tumor. Another group was injected intravenously with dendritic cells (derived from bone marrow by treatment with GM-CSF+IL-4 for 5 days (Mayordomo et al., 1995), incubated previously for 3 h with P815 texosomes. The tumors were measured and the results were analyzed as described in FIG. 6. The P815 texosomes sensitized the dendritic cells to induce the rejection of the established tumors. The microsomes had no significant effect on tumor growth. The insert shows the percentage of mice without tumor (along the ordinate), the filled bar corresponds only to the groups of animals of the filled squares type, time in days is shown along the abscissa. These mice did not develop tumors after reinjection of twice the minimal tumor dose, showing that they had developed an anti-tumor immunity. The symbols used in the figure are the following:

○: dendritic cells incubated with control texosomes,

■: dendritic cells incubated with P815 texosomes filled triangles: P815 texosomes injected intradermally x: untreated animals Time in days is indicated along the abscissa and the mean volume of the tumor is given along the ordinate.

FIGS. 8A, 8B and 8C. Cytotoxic/chemotherapeutic agents and irradiation may stimulate the exocytosis of the tumor texosomes.

Murine leukemia L1210 and the primitive human renal cancer line GIAM were used (FIG. 8C). Two million tumor cells were incubated in the presence of increasing quantities of 5-FU (in the case of L1210) or cis-platinum (CDDP) (in the case of GIAM) per ml for 16 hours.

The supernatant was recovered, then subjected to differential centrifugations as described in Table I.

GIAM was also incubated with 1000 IU/ml of IL-2 or dexamethasone ($10^{-6}$ M) or irradiated at 10,000 rads.

The high doses of chemotherapy and the irradiation are good examples of positive regulation of exocytosis of the texosomes in these tumor models. The results were also found in other tumors (FIGS. 8A and 8B); in particular, irradiation seems to be the most potent exocytosis stimulus.

FIG. 8A corresponds to the FON melanoma described above and FIG. 8B corresponds to a murine lymphoma designated EL4 (J. Nat. Cancer Ins. (1972) 48: 265–271).

The FON cells incubated under different conditions are shown in FIG. 8A:

1) CM: basic culture medium (RPMI containing 10% fetal calf serum)

2) DXM=in presence of dexamethasone, 3) irradiation: irradiated with 10,000 rads, 4) without serum, 5) IL-10=in the presence of IL-10, at 10 ng/ml.

The above irradiations are also valid for the EL4, L1210 and GIAM cells.

Figure 9A:
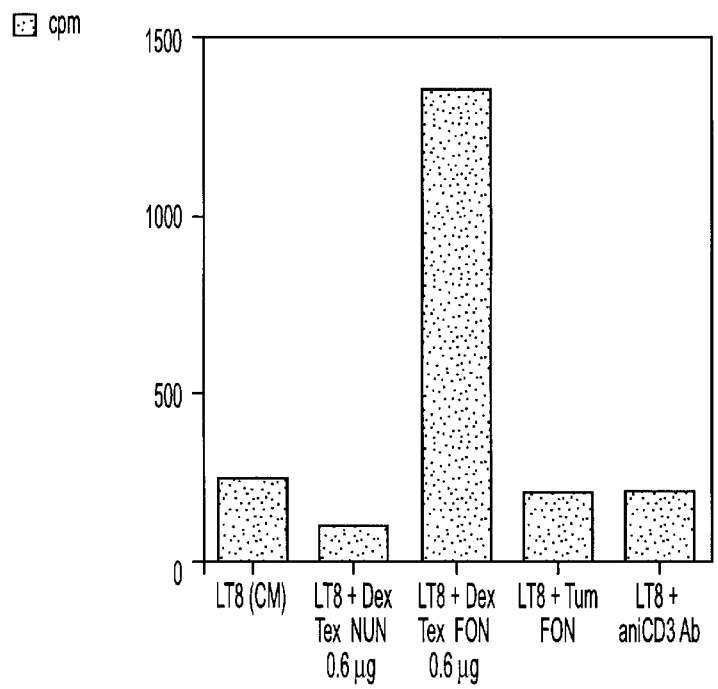
Figure 9B:
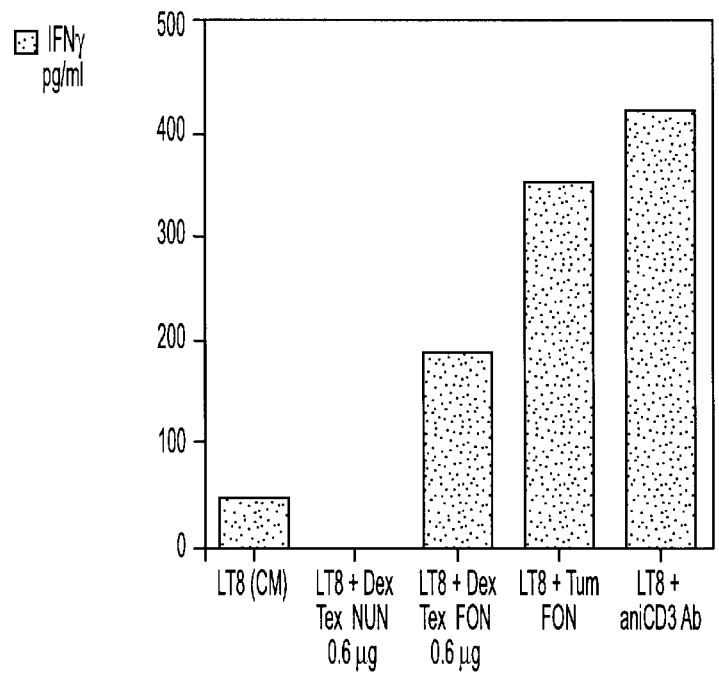
Figure 9C:
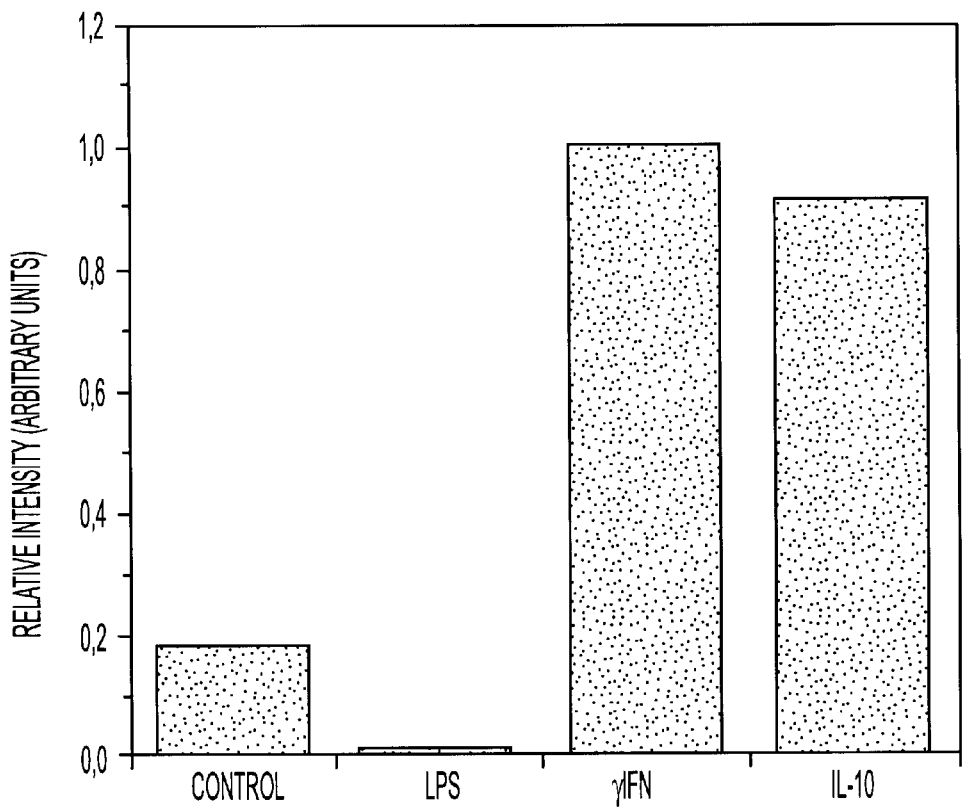

FIGS. 9A, 9B and 9C. The membrane vesicles (dexosomes) produced by the dendritic cells sensitized to melanoma tumor antigens are efficacious for stimulating the T lymphocytes specific for these melanoma, and their production is regulated by the cytokines.

LT8 (CM) corresponds to the LT8 T clones incubated in the basic culture medium as defined in FIG. 8A, DexTexNUN corresponds to the dexosome derived from dendritic cells loaded with texosome originating from NUN tumor cells, DexTexFON corresponds to the dexosome derived from dendritic cells loaded with texosome originating from FON tumor cells, TumFON corresponds to the FON tumor cells.

A. Proliferation assays: the FON texosomes (used in FIG. 3) were incubated with HLA-A2 dendritic cells for 3 hours, then washed with 9% saline solution and incubated in acidic medium pH 6.3 for 18 hours. The membrane vesicles of dendritic cells (dexosomes) are thus recovered from the culture supernatant of above-mentioned HLA-2 dendritic cells.

The membrane vesicles originating from dendritic cells loaded with texosomes (DexTex) are then incubated with the LT8 clones specific for MART-1 presented in the HLA-A2 context (the FON texosomes contain the antigen MART-1). The NUN texosomes (HLA-A2-negative renal cancer line, MART-1 negative) were used as negative control. The irradiated tumor line FON (Tum FON) or the anti-CD3 antibody, preabsorbed to plastic (anti-CD3Ab) was used as positive control. The incubation of the DexTex with the LT8 clones lasts 48 hours, then 1 µCi of tritiated thymidine is added per 200 µl well. The proliferations of LT8 lymphocytes are measured 18 hours later.

The counts per minute are shown along the ordinate.

B. Same operations but the IFNγ is measured in the culture supernatant by means of ELISA at 48 hours. The IFNγ content (pg/ml) is shown along the ordinate.

C. The dexosomes were isolated from dendritic cell supernatants after incubation for 48 hours in the presence or absence of LPS (20 µg/ml), IFN-γ (100 IU/ml) or IL-10 (10 µg/ml).

Figure 10A:
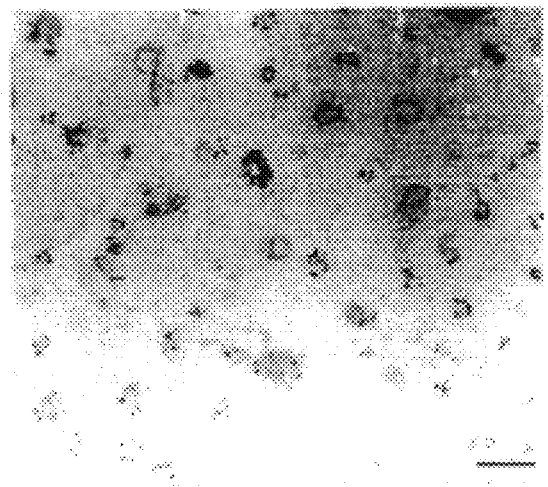

FIGS. 10A, B, and C. Micrographs of dexosomes in immuno-electron microscopy.

Figure 10B:
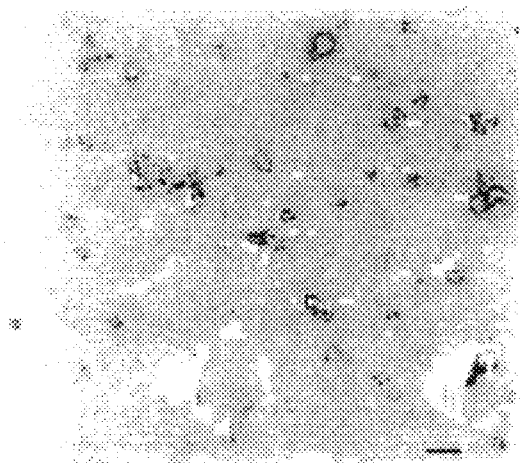
Figure 10C:
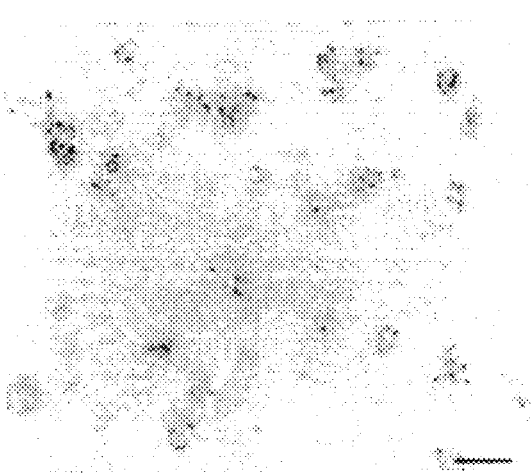

The dexosomes possess a homogeneous diameter included between 50 and 90 nm and are intensely labelled with anti-CD63 antibodies (FIG. 10A). The major portion of these dexosomes is also labelled with anti-MHC-I (page 15, FIG. 10B) and anti-MHC-II (page 15, FIG. 10C) antibodies. Bars: 250 nm.

Figure 11:
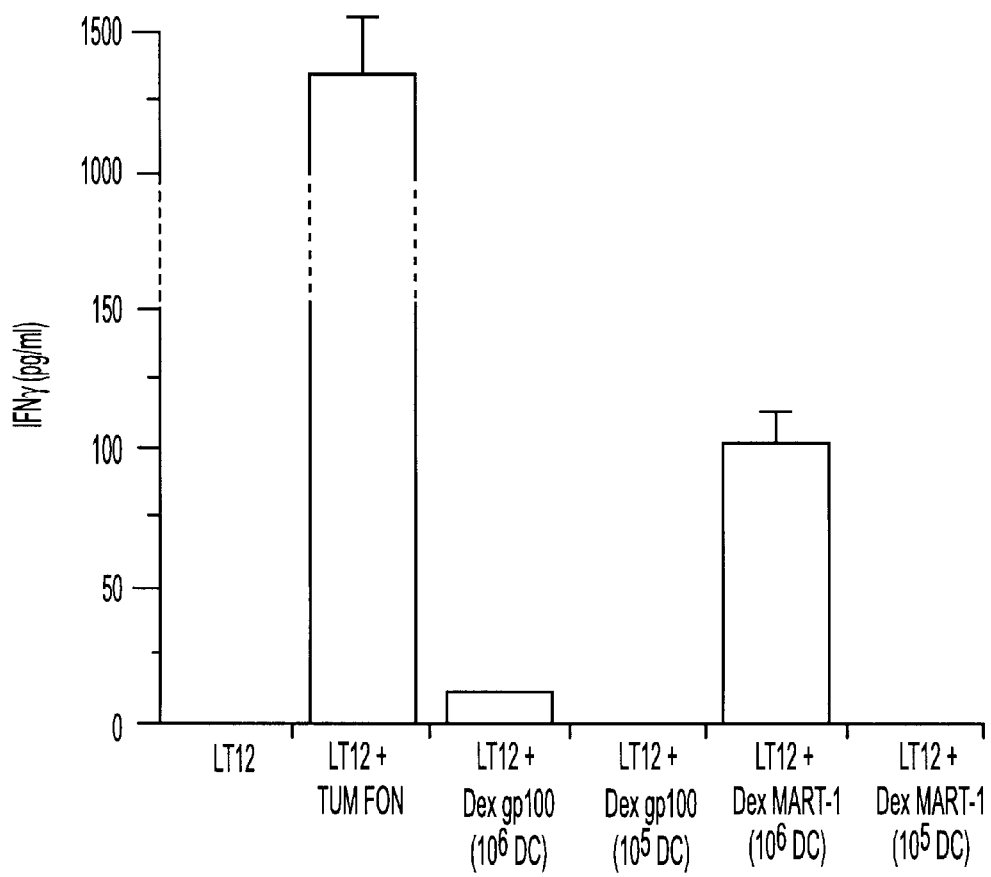

FIG. 11. Measurement of the levels of gamma interferon secreted by the T lymphocytes incubated in the presence of dexosomes loaded with peptides or control dexosomes. The dendritic cells (2×10⁶/ml) were incubated for 3 to 12 hours either in the presence of 10 µg/ml of the antigenic peptide MART-1/MelanA (27–35) or in the presence of 10 µg/ml of peptide gp100(280–288) (control) suspended in citric acid at pH 3.7, then the dexosomes were isolated. The cells of the LT12 clone (restricted HLA-A2 CTL clone, MART-1 (27–35) specific) were then incubated (100,000 CTL per well) with increasing doses of dexosomes or gp100 peptides (control in 96well plates for 5 days. The secretion of gamma interferon by cells was then measured by means of ELISA (Genzyme).

Figure 12:
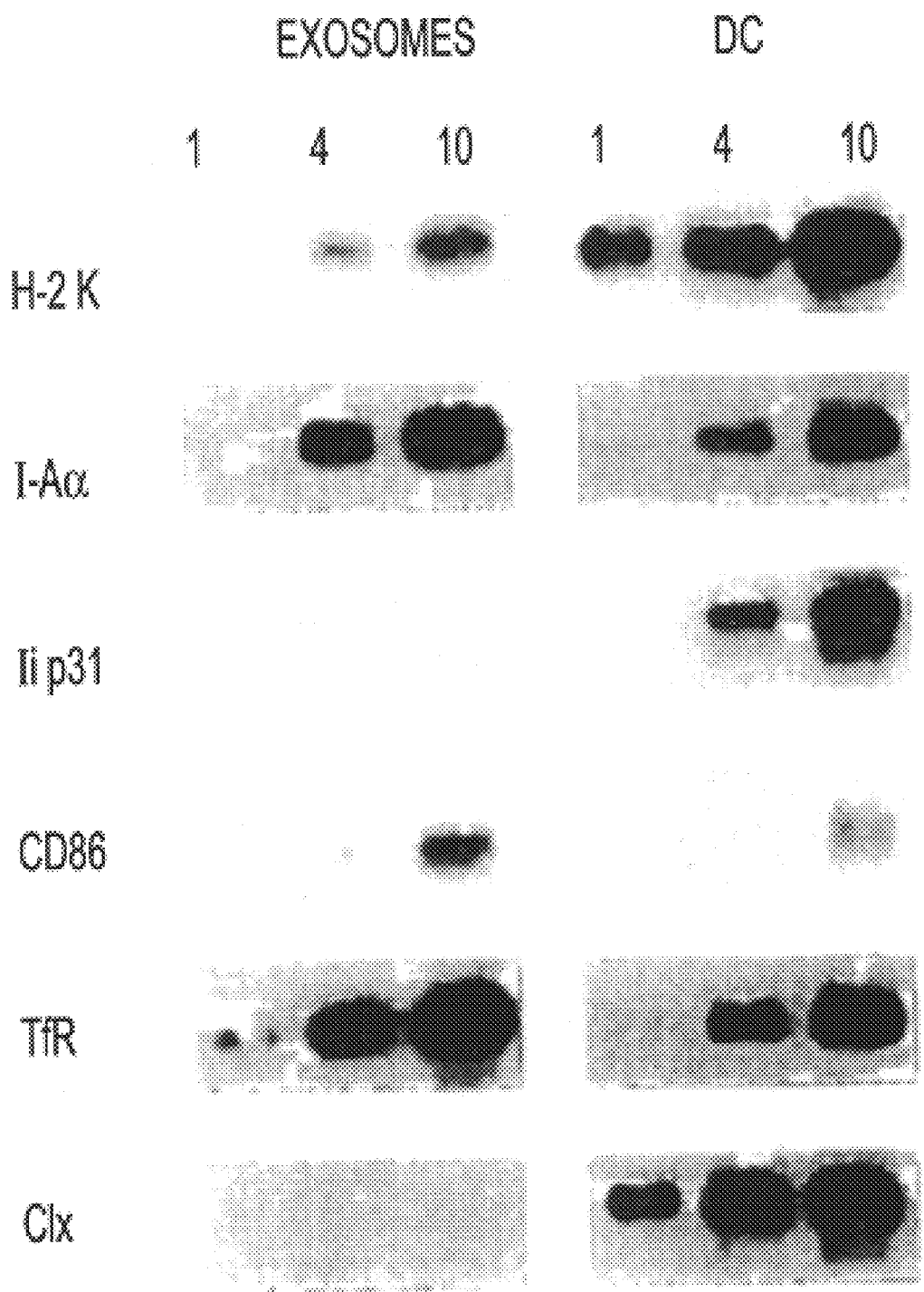

FIG. 12. Western blot analysis of the markers present on the dexosomes (1.4 and 10 µg) produced by dendritic cells derived from bone marrow: H-2K (MHC-1), I-Aα (MHC-II) CD86, CD63, TfR (transferrin receptor), Clx (calnexin), li p31 (invariable chain).

Figure 13A:
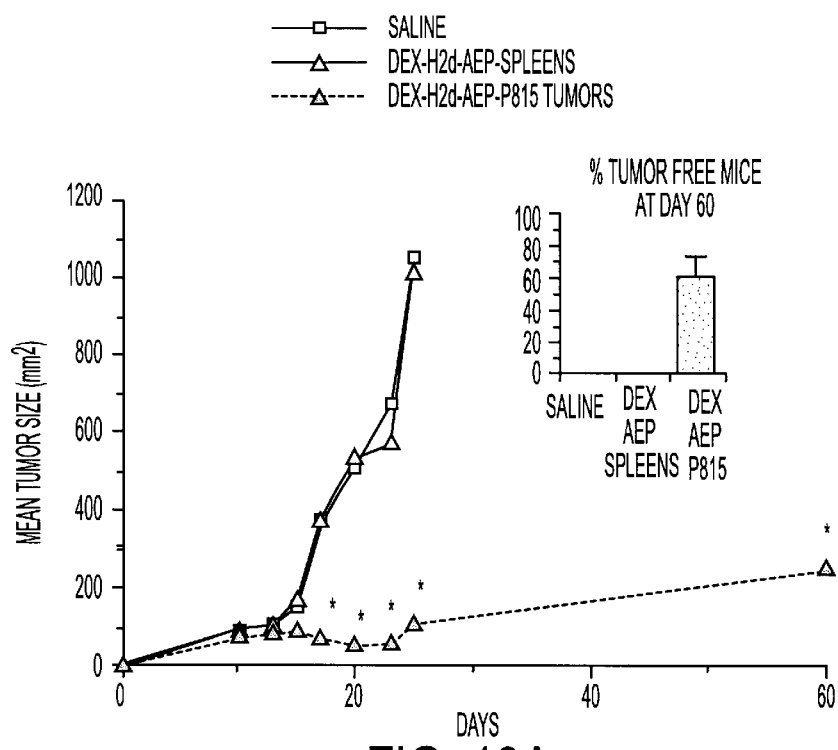

FIGS 13A and B. In vivo anti-tumor effect of the dexosomes on a mastocytoma (P815) tumor model. Dex-H2d-APE-P815: Dexosomes derived from dendritic cells of bone marrow loaded with an acidic petide eluate of the tumor P815. Dex-H2d-APE-spleens: dexosomes derived from dendritic cells of bone marrow loaded with an acidic peptide eluate of the spleen.

Figure 13B:
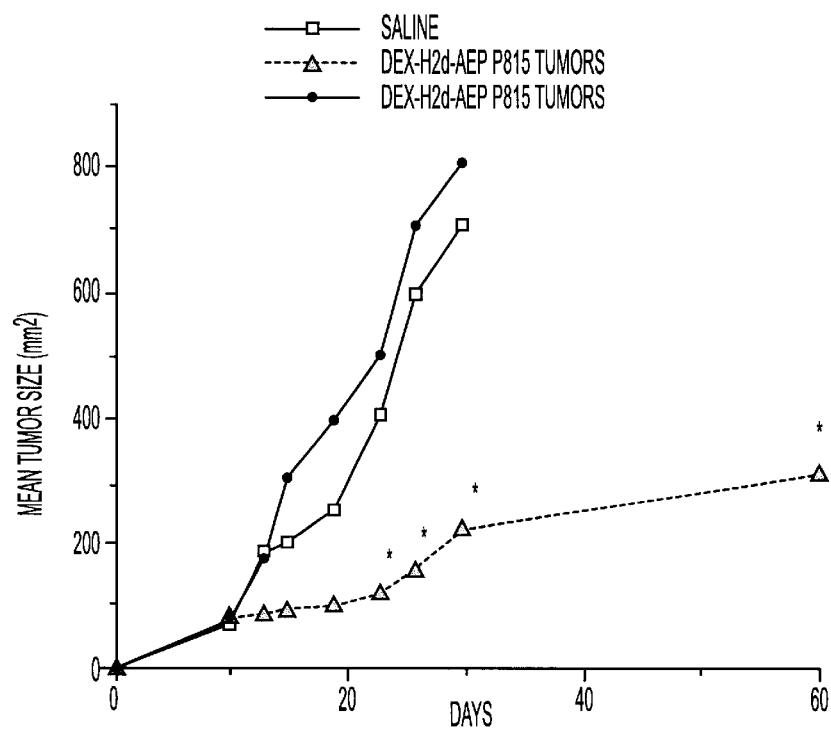
Figure 14A:
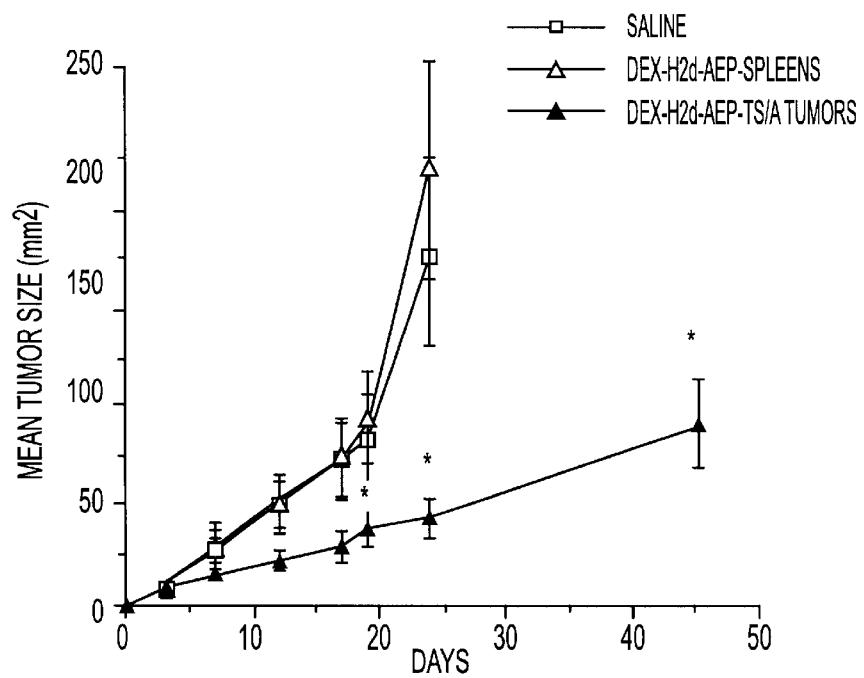

FIGS 14A and B. In vivo anti-tumor effect of the dexosomes derived from dendritic cells of bone marrow loaded with an acidic tumor peptide eluate on a mammary tumor model (TS/A). Legend: see FIG. 13. (A) Experiment performed on immunocompetent mice. (B) Experiment performed on Nude mice.

Figure 15A:
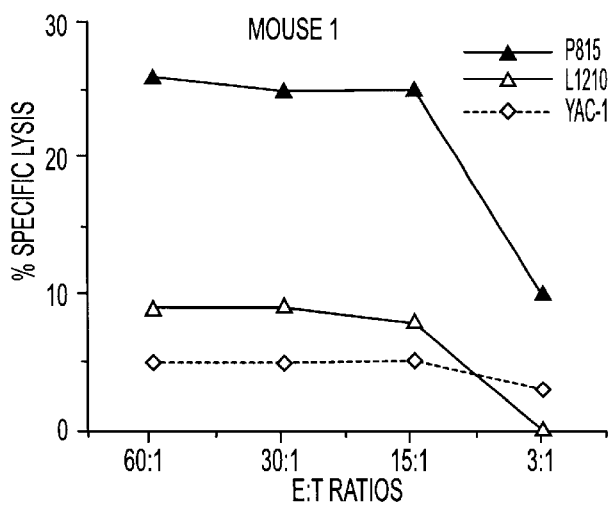

FIGS 15A, B, and C. Assay of release of radioactive chromium ($^{51}$Cr). This assay makes it possible to show that the dexosomes of the invention trigger a specific CTL response in vivo. Target cells: P815, leukemic line L1210, YAC line insensitive to NK cells.

Figure 16:
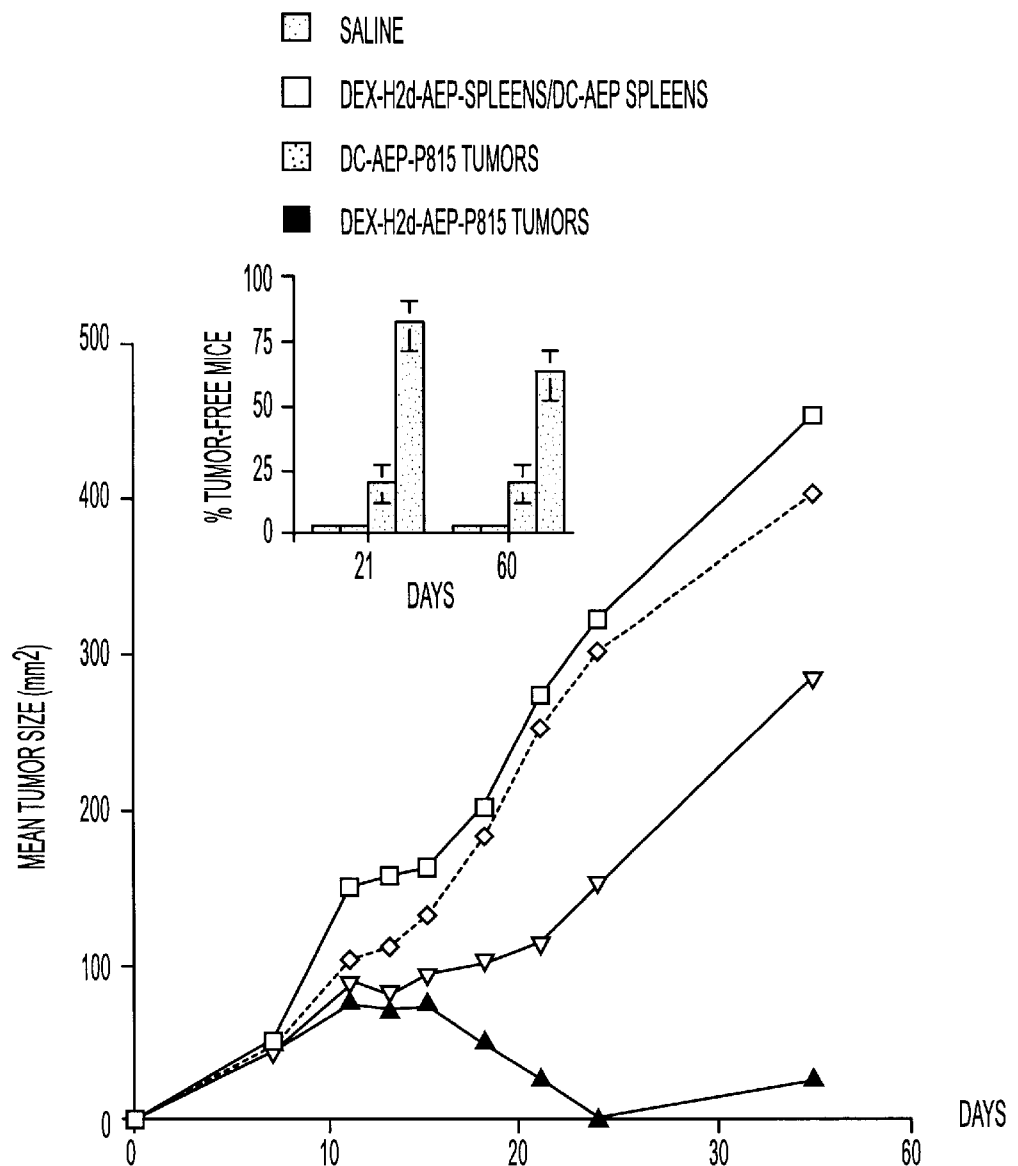

FIG. 16. Comparative efficacy of the dexosomes and the dendritic cells. This Figure shows that the dexosomes are more potent than the immature dendritic cells from which they are derived for the eradication of established tumors in vivo. Five million dendritic cells loaded with an acidic peptide eluate of the spleen (unfilled diamonds) or of the tumor P815 (unfilled triangles) were administered by the intravenous or intradermal route to mice with established P815 tumors at day 8 to 10. In parallel, the supernatant of these cells was harvested after incubation for 18 h with the peptides of the spleen (unfilled diamonds) or of tumor P815 (filled triangles), ultracentrifuged and characterized with respect to its dexosome content. Five million dendritic cells enabled 5 to 10 µg of dexosomes to be obtained, which allowed the immunization of 5 mice by intradermal administration in the same flank. A single administration of dexosomes was performed on days 8–10. The size of the tumors was measured twice a week and is shown on the Figure. * represents results with 95% significance according to the exact method of Fisher, in comparison with the injections of saline solution (unfilled squares) or pulsed dendritic cells. Inset are shown the percentages of mice immunized against P815 showing a total absence (disappearance) of tumor during (day 21) and at the end (day 60) of the experiment in the different groups of 5 mice.

Figure 17:
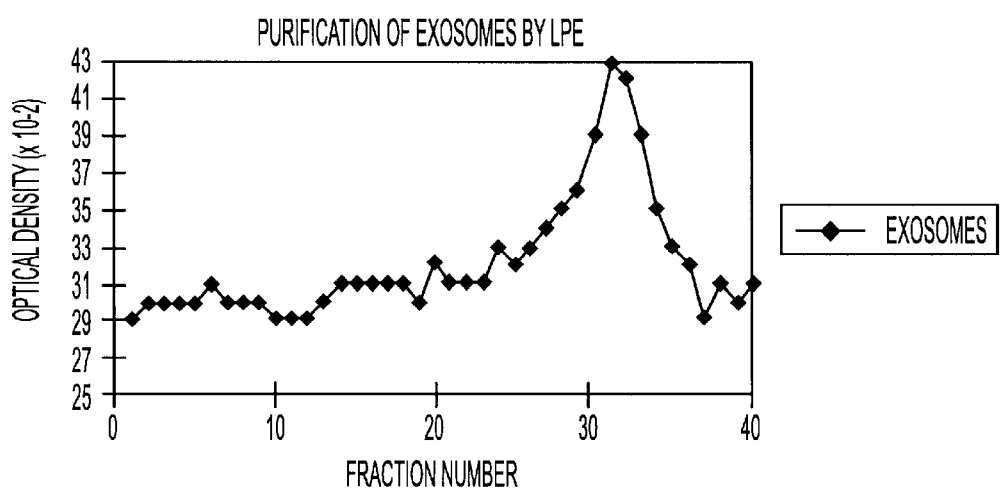

FIG. 17. Purification of the dexosomes by liquid phase electrophoresis.

EXAMPLES

1. Production of Texosomes by Murine and Human Tumor Cell Lines

This example illustrates the capacity of tumor cells to produce lipid vesicles.

These murine or human tumor cells originating from leukemias or solid tumors (renal or colon melanoma) (see Table 1) were incubated for 24 h at a density of a million cells per milliliter. The culture medium (RPMI containing 10%o fetal calf serum) was then freed from cells by centrifugation at 300 g for 10 minutes. The cellular debris were then removed by two successive centrifugations, each for 15 minutes at 800 g (and an optional centrifugation for 30 minutes at 10,000 g). The texosomes were finally recovered by centrifugation for 60 minutes at 100,000 g, then washed once with PBS under the same conditions. The protein concentrations in the texosome preparations was measured by the Bradford method (BioRad Protein Assay {BioRad}).

All of the tumor lines tested, human and murine (solid or hematopoietic, primary or established in culture or originating from dissociated fresh tumors) produce texosomes (Table 1). However, the efficacies of production vary between the different lines. The murine tumor cell lines produce between 100 and 200 micrograms of texosome proteins per 50 million cells in 24 hours. The human melanoma and nephroma lines produce between 10 and 100 micrograms of texosome proteins per 20 million cells in 24 hours.

2. The Vesicles Produced by the Tumor Cells are of Endocytic Origin

In order to determine whether the vesicles purified from the supernatants of the tumor cell lines are of endocytic origin, we have carried out a morphological study by means of the electron microscope of one of these tumor lines, TS/A (mouse mammary carcinoma line) (Nanni P. et al. (1983) "TS/A: a new metastazing cell line originating from a BALB/c spontaneous mammary adenocarcinoma" Clin. Exp. Metastasis 1: 373–380). The tumor cells were fixed and prepared for electron microscopy as previously described. The texosomes were deposited directly on grids and analyzed.

Figure 1B:
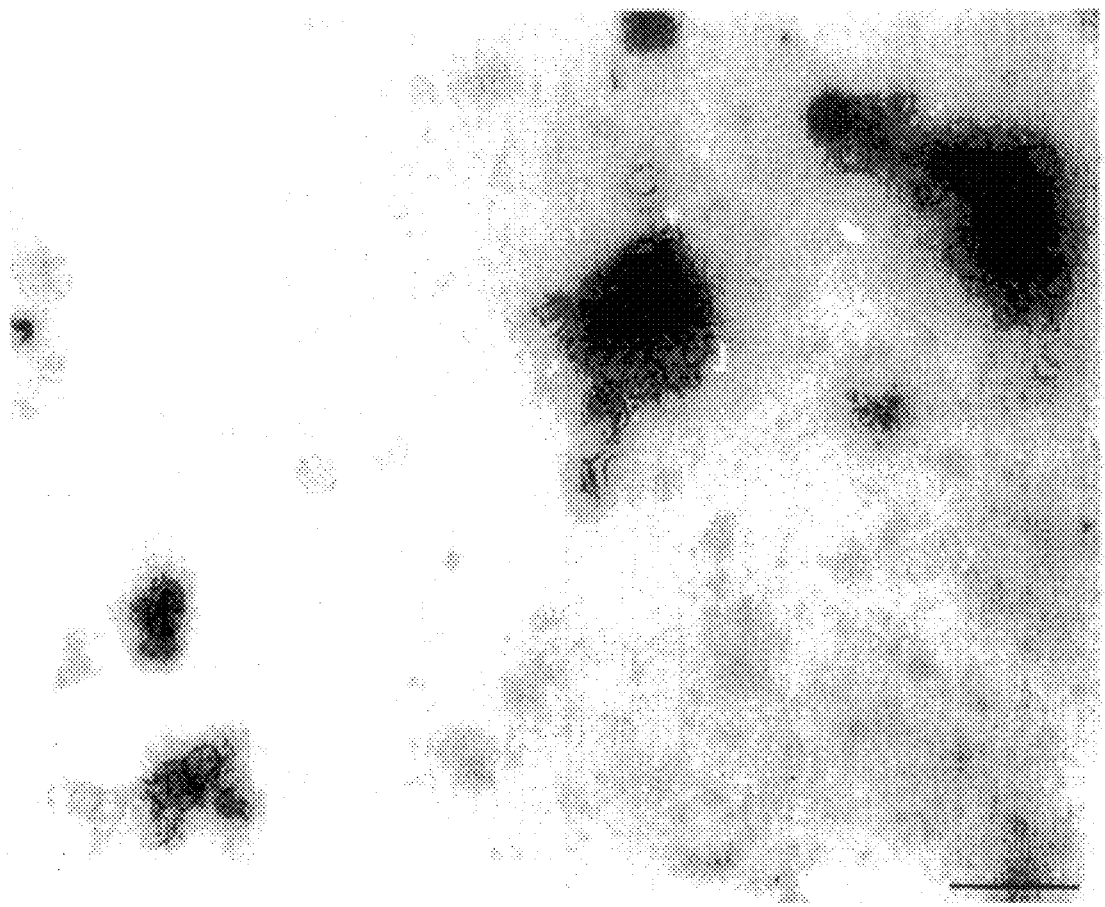

FIG. 1A shows examples of intracellular compartments of multivesicular appearance observed in the tumor cells. These endocytic compartments are 200–300 nm in diameter (the bar at the bottom of the panels A and B represents 200 nm) and are composed of an external membrane surrounding multiple internal vesicles 68–80 nm in diameter. The texosome preparations contain a major population of vesicles 60–80 nm in diameter (FIG. 1B), sometimes as aggregates and morphologically similar to the internal vesicles of the multivesicular endosmes observed in the interior of the cells (FIG. 1A). These results suggest that the texosomes are secreted into the extracellular medium after fusion of the external membrane of the endosomes with the cytoplasmic membrane. In fact, such exocytosis profiles are observed in these cells (data not shown).

In order to determine whether the texosomes are actually of endocytic origin, a Western blot analysis was then carried out on the markers present defined below in the texosomes derived from tumor lines TS/A and P815 (mastocytoma data by T. Boon, Ludwig Institute, Brussels, Belgian) (murine mastocytoma). In order to do this, two micrograms of texosome proteins or the cell lysate of 200,000 TS/A cells were separated by polyacrylamide gel, then transferred to a Nylon membrane (Amersham). The possible presence of different markers was then revealed with the aid of specific antibodies. The texosomes of TS/A and P815 contain class I molecules of the MHC, as well as different markers of the endocytic pathway (the transferrin receptor, the lysosomal glycoproteins Lamp 1 and 2) (FIG. 1A). On the other hand, a marker characteristic of the endoplasmic reticulum (ER), calnexin, is not present in the texosome preparations, showing that ER membranes do not contaminate the texosomes.

3. The Texosomes Produced by a Melanoma Line Contain a Cytosolic Tumor Antigen These results show that the texosomes secreted by the tumor cells correspond to the internal membranes of the multivesicular endosomes. Now, these intraendosomal vesicles are formed by invagination, followed by budding from the external membrane of the endosomes towards the interior of the endosome. These intraendosomal vesicles and, consequently, the texosomes ought to contain a cytosol fraction. This is particularly important in the context of anti-tumor immunotherapy, since some tumor antigens, including MART-1 (one of the most studied) are cytosolic proteins. Hence the presence of MART-1 in the texosomes has been assayed.

In order to do this, ten micrograms of texosome proteins or the cell lysate of 200,000 cells of a human melanoma line (M10) (T. Boon, Ludwig Institute, Brussels, Belgium) were analyzed by Western blot, as previously. The possible presence of MART-1 was then revealed with the aid of specific anti-MART-1 antibody (S. Rosenberg, NCI, Bethesda, U.S.A.). The texosomes secreted by the FON tumor line (melanoma from the patient FON obtained from F. Faure, Pasteur Institute, Paris, France) contain the tumor antigen MART-1. Protection experiments with proteinase K (Sigma) showed that the MART-1 epitope recognized by this monoclonal antibody is in the interior of the texosomes (results not shown).

This first part of the work shows that:
- the tumor cells produce and secrete vesicles,
- these vesicles are, vesicles of endosomal origin comprising an external membrane on which are found different membrane molecules (class I of the MHC, different endosomal markers),
- these vesicles contain a cytosol fraction, including cytosolic tumor antigens, like MART-1.

These results have led to the verification of the following biological activities of the vesicles, designated texosomes.

4. The Texosomes can Stimulate CD8 T Lymphocytes in Vitro

Since the texosomes bear class I molecules at their surface, it has been assayed whether they are capable of stimulating CD8 T lymphocytes. Two T clones were used, LT8 and LT12, donated by F. Faure, Pasteur Institute, Paris, France, which recognize a peptide derived from MART-1 in combination with HLA-A2 (Dufour et al., 1997). For this purpose, since the FON tumor cells are HLA-A2, the cells of the LT8 or LT12 T clones were incubated with texosomes prepared from FON supernatants or, as a positive control, intact FON cells. The activation of the T lymphocytes was measured by the secretion of TNFβ. The FON texosomes induced the secretion of TNFβ by LT8 and LT12 in a dose-dependent manner (FIG. 3). The FON cells also induced TNF secretion, whereas texosomes derived from tumor cells not expressing MART-1 do not?(FIG. 3).

Hence, HLA-A2/MART-1 peptide complexes are present at the surface of texosomes.

Similar results were obtained in the mouse with spleen lymphocytes of a mouse immunized by β-galactosidase (β-gal).

Texosomes were produced from supernatants of P815 mastocytoma cells or P815 cells expressing β-gal (lines obtained from A. Albina, Gustave Roussy Institute, Villejuif, France) or of cells of another tumor (L1210) H2α murine leukemia) not expressing β-gal, L210. Increasing concentrations (0.3 μg/ml to 20 μg/ml) of these different texosome preparations were then incubated for 4 days with spleen cells of mice immunized with β-gal expressed in a recombinant adenovirus. Only the texosomes of P815 cells (at the highest concentration of 20 μg/ml) expressing β-gal induced significant, although quite moderate, proliferation (see FIG. 4) (measured by tritiated thymidine incorporation) of the spleen cells. These results show that the texosomes produced by the P815 cells expressing β-gal bear at their surface complexes of H2α/peptides derived from β-gal and are capable of activating murine T lymphocytes.

5. The Texosomes Can Deliver Cytosolic Antigens Which They Contain to Antigen-presenting Cells to be Presented to the T Lymphocytes For this purpose the LT8 and LT12 T clones recognizing specifically a peptide derived from MART-1 (MART-127-35=AAGIGILTV (SEQ ID NO. 1), Dufour E. et al., Diversity of the cytotoxic melanoma-specific immune response. J. Immuol. 1997, 158: 3787–3795) were used in combination with HLA-A2. It has been shown that the texosomes produced by the FON human melanoma line (which is HLA-A2) contain the tumor antigen MART-1 (see FIG. 2) and are capable of activating directly the clones LT8 and LT12. In order to dispose of texosomes also containing MART-1, but incapable of stimulating the clones LT8 and LT12 directly, the MZ2 melanoma line was used (T. Boon, Ludwig Institute, Brussels, Belgium), MART-1-positive but expressing a restriction element other than HLA-A2 (in fact, HLA-A1). In fact, the MZ2 cells, as well as the texosomes derived from these cells, do not activate the clones LT8 and LT12 (results not shown), unlike the FON cells and the texosomes derived from these cells (FIG. 3). On the other hand, when these same texosomes derived from MZ2 are incubated in the presence of dendritic cells expressing HLA-A2, stimulation of the T clones LT8 and LT 12 is observed as in the case of the texosomes drived from FON (FIG. 5).

In the case of texosomes derived from MZ2, the activation of the T clones can not be due to pre-existing complexes of HLA-A2/peptides derived from MART-1 since they do not express the appropriate restriction element (HLA-A2). Consequently, it can only be the antigen contained in the texosomes which was taken up by the antigen-presenting cells and degraded to peptides which are then combined with the HLA-A2 molecules of the presenting cell. The texosomes thus permit the transfer of an antigen between a tumor cell and an antigen-presenting cell. The texosomes thus have a function similar to that of "natural liposomes".

6. The Texosomes Induce the Regression of Solid Tumors Established in Vivo

Finally, since the texosomes are capable of stimulating T lymphocytes in vitro and of sensitizing dendritic cells for the activation of tumor-specific T lymphocytes, the anti-tumor activity of the texosomes was tested in vivo.

In order to analyze such an anti-tumor activity, mice were injected with twice ($10^5$) the minimal tumorogenic dose of tumor cells of a mammary tumor (TS/A cells of H2d haplotype, syngeneic with BALB/c cells) in the flank. After 3 or 4 days, the animals with established tumors were injected twice (day 3 or 4) with texosomes prepared from TS/A cell supernatants or texosomes from MC38 cells as negative control (S. Rosenberg, NCI, Bethesda, U.S.A.) (tumor cell of H2b haplotype) or a similar volume of PBS. The mean size of the tumors in the group of mice inoculated with TS/A texosome preparations is very diminished in comparison with the groups of control mice. This anti-tumor effect is dependent on T cells, since Nude mice (mutant mice lacking T lymphocytes) bearing the tumor and inoculated similarly with texosome preparations do not show diminution of the tumor mass (FIG. 6B).

In this same series of experiments, an anti-tumor effect was observed with texosomes prepared from P815 mastocytoma cells of the H2d haplotype which suggests that these two tumors express common antigens. Similar results were obtained with another very immunogenic tumor model, the mastocytoma P815 (syngeneic with DBA/2 mice and of H2d haplotype). In this model, it was shown that texosomes injected intradermally in the flank of a mouse bearing an established tumor (P815) on day 10 (tumor measuring 80–100 mm$^2$) have the capacity to bring about the eradication of the tumor in more than 60%o of the cases. Furthermore, these mice show an anti-tumor immunity in the long term (results not shown). In this series of experiments, anti-tumor effects of texosomes prepared from L1210 lymphocytes isolated from a murine leukemia of H2d haplotype and TS/A cells were observed, which indicates that common epitopes also exist between these three tumors (mutated p53 is common to the two tumors P815 and TS/A).

The anti-tumor effect of the texosomes might be explained by two mechanisms.

First, once injected, the texosomes might activate the tumor-specific T lymphocytes of the host directly. In this manner, a clonal expansion of tumor-specific T lymphocytes or a "priming" of the T cells might take place. A second hypothesis implicates a direct interaction of the texosomes injected with the dendritic cells of the host. This might then stimulate the anti-tumor response. In order to test this second hypothesis, the growth of tumors in mice injected intravenously with dendritic cells derived from the bone marrow loaded with texosomes from tumor cells was monitored. DBA/2 mice (IFFA CREDO, Orleans, France) were thus injected with twice ($50\times10^5$) the minimal tumorigenic dose of P815 mastocytoma cells. Ten days later, each animal was injected with $5\times10^5$ dendritic cells loaded, and as a result sensitized, with 9 $\mu$g of texosomes. The mean size of the tumors under these conditions significantly diminishes in comparison with groups of mice injected with PBS or with dendritic cells loaded with texosomes of cells of a control tumor MC38. In fact, more than 60% of the animals treated no longer had a tumor at the end of the experiment. Furthermore, relapses were not observed in the long term (in 80%o to 100% of the cases). It is interesting to observe that such a sub-optimal dose of texosomes injected intradermally has no effect, which suggests that the dendritic cells may prepare dexosomes containing the tumor antigens much more efficaciously than the dendritic cells of the dermis or Langerhans cells. Similar results were obtained with the model of the breast tumor TS/A cells.

The results obtained in the framework of the invention show that the texosomes sensitize the dendritic cells efficaciously. These cells thus sensitized have the capacity to induce potent anti-tumor responses in vivo in the cases of different tumors. These results suggest that the anti-tumor effects observed after direct inoculation of texosomes in vivo are due to the sensitization of the dendritic cells of the host. Remarkably, the effect is observed after a single injection of sensitized dendritic cells. The majority of the treated mice show a complete tumor regression or prolonged survival (60 days versus 20 days in the control) due to tumor regression.

The method of sensitization of the presenting cells of the invention possesses different advantages over the methods of the prior art:
i) it does not require prior knowledge of tumor antigens: that is particularly important since tumor antigens are not known in the vast majority of tumors;
ii) the process of the invention can be applied to any4tumor whatever which produces texosomes; of the more than 15 tumor cell lines tested so far, only one did not produce texosomes (one of six melanoma lines tested).
iii) this method does not depend on the haplotype of the MHC of the patient and the tumor cells, since the tumor antigens present in the texosomes are re-prepared and presented to the T lymphocytes by molecules of the MHC of the antigen-presenting cells of the patient;
iv) the process of the invention can in principle be efficacious between tumors of different origins since there exist tumor antigens common not only to a particular type of tumor (MART-A for example in melanoma) but also antigens common to completely different tumors (like the molecules implicated in tumorigenesis, p53 for example);

v) the use of texosomes may also prove to be efficacious in the treatment of tumors expressing low levels of class I molecules of the MHC or not expressing them at all (these tumors represent 40–50% of human metastatic cancers). In fact, the texosomes permit the transfer of intact antigens between tumor cells and dendritic cells, these antigens then being presented to the T lymphocytes by the MHC molecules of the dendritic cell. The preliminary results show that the texosomes induce the rejection of murine tumors expressing low levels of class I molecules of the MHC (like MCA101, S. Rosenberg, NCI, Bethesda, U.S.A.). This probably is due to the fact that the expression levels of the molecules of the MHC necessary for the induction of an efficacious immune response are much higher than those necessary during the effector phase (cellular cytotoxicity);

vi) the texosomes alone themselves constitute a novel and efficacious method of prophylactic or therapeutic vaccination as a result of their immunogenic potency.

7. The Dendritic Cells Produce Immunogenic Membrane Vesicles (Dexosomes)

This example demonstrates that the dendritic cells produce membrane vesicles and that these vesides constitute potent immunogenic vesicles for anti-tumor immunization. These vesicles are particularly advantageous since they make it possible to avoid the in vivo injection step of the whole dendritic cells from which they originate.

The dendritic cell therapy does not offer the certainty of the stable phenotype of the cell injected nor of the homogeneity of the cellular compositions used. By administering a stable product secreted by these cells, i.e. the above-mentioned membrane vasicles, a guarantee is offered to the tumor-bearing host of efficacy and immunizing potency.

In this example, dendritic cells derived from bone marrow by treatment for 5 days with GM-CSF+ILA (Mayordomo et al., 1995) were incubated for 3 hours with tumor cell exosomes. The cells thus sensitized were then cultured in acidic medium for 18 hours (in order to stimulate the production of vesicles), then vesicles were observed and harvested according to the methodology described in Example 1. In order to determine their immunogenic potency, these vesicles were then incubated in vitro with cytotoxic T lymphocytes specific for the MART-1 antigen. The results presented in FIG. 9 show that 0.6 µg of these membrane vesicles, called DexTexFON (i.e. dexosome originating from dendritic cells incubated with texosomes derived from FON tumor cells) make it possible to stimulate directly the proliferation and secretion of IFNγ from LT8 clones specific for MART-1 and this is what 0.6 µg of dexosomes originating from dendritic cells incubated with texosomes of NUN tumor cells: DexTexNUN (NUN being a renal tumor, HLA-A2 negative, MART-1 negative) cannot do. These results thus show (i) that the dendritic cells produce membrane vesicles and that these membrane vesicles constitute a potent immunogen.

In addition, the result presented in FIG. 9C show that, unexpectedly, the production of dexosomes for the dendritic cells is a regulated phenomenon, which may be stimulated in the presence of certain cytokines such as IFN-γ and IL-10. Thus, the results presented show that IFN- or IL-10 significantly increase (by about a factor of 5) the production of dexosomes. Comparable results were observed with IL-12.

8. Characterization of the Membrane Vesicles Produced by the Dendritic Cells The capacity of the dendritic cells to produce membrane vesicles was first confirmed on dendritic cells produced from human monocyte precursors and on the murine D1 dendritic cell line.

The D1 cell line and the conditions of maturation of this line have been described by Winzler et al. (J. Exp. Med. 185 (1997) 317).

The dendritic cells derived from human monocyte precursors were obtained from the adherent fraction of mononucleated cells, taken from healthy subjects, incubated for 7–8 days in AIMV medium containing L-Glu, antibiotics, 1000 IU/ml of rhGM-CSF and rhIL-4 (Schering Plough, Kenilworth, N.J., USA). After being cultured for 8 days the wealdy adherent cells and the cells in suspension exhibit a typical morphology of dendritic cells, express high levels of MHC molecules I and II as well as CD40 and CD86.

The major portion of these cells is positive for CD1a and CD11b and negative for CD2, CD3, CD14, CD19 and CD83.

The microscopic analyses of these cells revealed the presence of membrane vesicles rich in MHC molecules I and II. These vesicles were isolated by centrifugation and analyzed by means of immuno-electron microscopy. More particularly, the culture supernatants of the dendritic cells were harvested, centrifuged at 300 g for 20 minues, then at 10,000 g for 30 minutes at 4° C. in order to remove the cells and cellular debris. The dexosomes were then isolated by centrifugation at 100,000 g for 1 h at 4° C., followed by washing with PBS under the same conditions (centrifugation at 100,000 g for 1 h at 4° C.). The protein concentration in the dexosome preparations was measured by the Bradford method (BioRad Protein Assay {BioRad}).

The results obtained show (FIG. 10) a homgeneous population of vesicles having a diameter induded between about 60 and 90 nm. Moreover, more than 95% of the dexosomes are labelled by anti-CD63, anti-CD82, anti-MHC-I and anti-MHC-II antibodies.

These results confirm that the dendritic cells produce membrane vesicles exhibiting antigen-presenting molecules as well as lymphocytic costimulatory molecules.

9. The Dexosomes Present the Antigens in a Restricted MHC-I Context

One of the advantageous characteristics of the dexosomes resides in the presence of class I molecules of the MHC. These molecules are in fact necessary for the generation of an efficacious cellular response, and in particular for the activation and expansion of CPL cells. The capacity of the dexosomes to stimulate the CD8+ lymphocytes and the specific character of the lymphocytes obtained have thus been tested.

To do that, the dendritic cells obtained from human monocyte precursors (HLA-A2 subjects) were first sensitized to a particular antigen by "peptide pulsing". For this purpose, the cells ($2 \times 10^6$/ml) were incubated for 3 to 12 hours, either in the presence of 10 µg/ml of the antigenic peptide MART-1/MelanA(27–35), or in the presence of 10 µg/ml of peptide gp100(280–288) (control) in citric acid suspension at pH 3.7. After this sensitization step, the dexosomes were isolated as described in Example 1. The cells of the LT12 clone (restricted CTL clone HLA-A2, MART-1(27–35) specific) were then incubated (100,000 CTL per well) with increasing doses of dexosomes or peptide gp100 (control) in 96 well plates for 5 days. The secretion of gamma interferon by the cells was then measured by ELISA (Genzyme).

As shown in FIG. 11, the dexosomes bearing the peptide MART-1 are capable of stimulating the production of gamma interferon by the clone LT12 in a dose-dependent manner. On the other hand, the dexosomes produced from the dendritic cells pulsed with the control peptide gp100 exert no stimulating effect on this clone.

These results confirm that the molecules of MHC-I expressed by the dexosomes of the invention are functional.

10. The Dexosomes Block Tumor Growth In Vivo

This example demonstrates the capacity of the dexosomes of the invention to induce an immune response in vivo and more particularly to induce the proliferation of tumor-specific T cells.

Dendritic cells obtained from bone marrow were loaded with an acidic tumor eluate containing different tumor antigenic peptides. The preparation and sensitization technology for the dendritic cells has been described by Zitvogel et al. (1996). FIG. 12 shows the markers expressed by the dexosomes produced by these dendritic cells. As indicated previously, this figure shows the abundant presence of class I and class II molecules of the NHC as well as the markers CD86 and the transferrin receptor. On the other hand, although they appear in the cell lysates, the markers H2-M, li and calnexin are undetectable in the exosomal preparations.

Two experimental tumor models were selected to test the in vivo anti-tumor properties of the dexosomes of the invention. The first model, P815, is an aggressive mastocytoma syngeneic with DBA/2 (H2d) for which very few efficacious immunotherapies have been reported on established tumors at day 10. The TS/A model is a weakly immunogenic spontaneous mammary carcinoma expressing lower levels of class I molecules of the MHC, syngeneic with BALB/c (H2d). The tumor peptides of the tumors P815 or TS/A eluted by acidic treatment were loaded on to the syngeneic dendritic cells, derived from bone marrow as previously described. The dexosomes were then prepared from these dendritic cell supernatants and used for in vivo immunization.

Mice and Tumor Cell Lines

DBA/2J (H2d) and BALB/c (Hcd) female mice six to eight weeks old were purchased from the Iffa Credo Laboratory, Lyon, France and housed under pathogen-free conditions. The nude mice were housed in a protected micro-environment. The P815 cells were provided by T. Boon (Ludwig Institute, Belgium). The TS/A model was furnished by Guido Forni (Immunogenetic and Histocompatibility Center, Turin, Italy). All of the tumor lines were stored in RPMI 1640 medium supplemented by 10% fetal calf serum endotoxin-free (Gibco BRL), 2 mM of L-glutamine, 100 unitd/ml of penicillin, 100 mg/ml of streptomycin, essential amino acids and pyruvate. This medium is also designated in what follows as CM medium.

Protocol and Results

Twice the minimal tumorigenic dose of tumor cells ($5 \times 10^5$ P815, 105 TS/A) were inoculated intradermally into the upper region of the right flank of the DBA/2 and BALB/c mice, respectively. The animals presenting three to four days established TS/A tumors or six to ten days established P815 tumors were then immunized by a single intradermal injection of 3 to 5 $\mu$g of dexosomes in the lower region of the same flank. These procedures were performed in a similar manner on both the immunocompetent animals and on the nude mice. A single therapeutic injection was performed for each mouse. The size of the tumors was checked twice a week and the mice were sacrificed when the tumors they bore were ulcerated or too large. Each series of experiments was performed two or three times by using groups of five mice for each individual treatment. The results obtained are presented in FIG. 13. As is shown in FIG. 13B, the treatment of established P815 tumors on day 10 (having a size of 50 to 90 mm²) could be achieved by a single intradermal administration of 3 to 5 $\mu$g of dexosomes per mouse. Within one week, tumor growth is stopped in the groups which received the dexosomes derived from dendritic cells loaded with the autologous tumor peptide and in 40 to 60% of the mice the tumors had disappeared completely at day 60.

Moreover, these animals exhibit a lasting immune response and rejected an additional injection of P815 normally lethal for untreated mice. On the other hand, these mice are not protected against an injection of the syngeneic leukemia clone L1210, which shows clearly the immuno-specific character of the effect obtained. Finally, the groups of mice immunized with control dexosomes (loaded with peptides of the spleen of mice) exhibit no anti-tumor effect as do untreated mice. These result show therefore that the dexosommes loaded with tumor peptides according to the invention are capable of inducing a regression of the tumor in vivo.

Figure 14B:
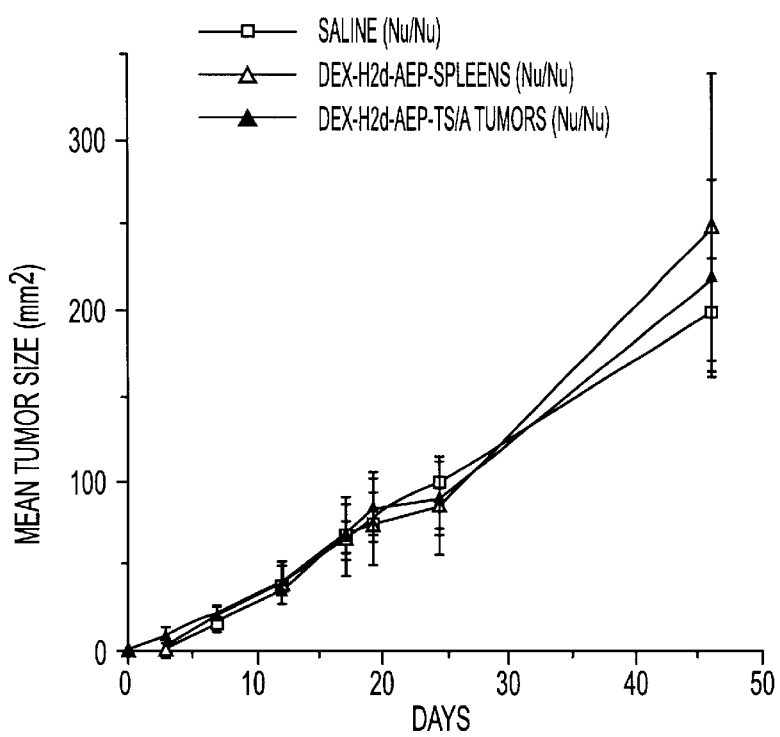

Similar anti-tumor effects were obtained with the TS/A tumor model comprising established tumors at days 3/4. In this series of experiments, all of the mice showed a statistically significant delay in tumor growth which prolonged their survival (FIG. 14). This anti-tumor effect was not observed in Nu/Nu athymic mice as indicated in FIG. 14B, which shows that the presence of T cells is necessary for the expression of the anti-tumor effect of the dexosomes of the invention.

Figure 15B:
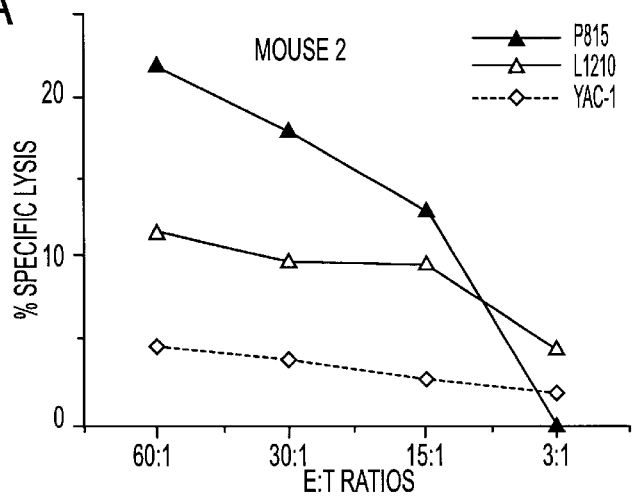
Figure 15C:
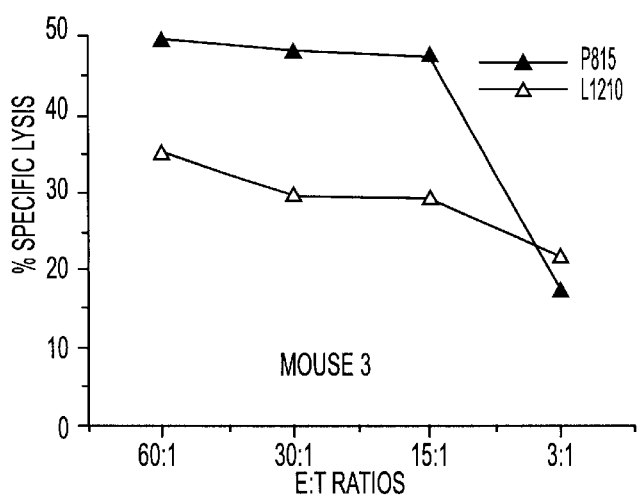

Furthermore, the following experiment shows that the dexosomes stimulate directly a specific CiL response in the animals presenting the tumor P815. The splenocytes of mice which had rejected the P815 tumors after immunization with dexosomes were harvested on day 90 and cultured for five days in the presence of irradiated P815 cells expressing the antigen B7.1 to enhance the frequency of specific precursors. These effector cells were tested in a chromium-release assay against (i) the autologous P815 (H2d) tumor cells,(ii) the unrelated L1210 cells and (iii) the YAC cells. A significant specific cytolytic activity was observed against the P815 cells in the splenocytes of mice immunized with the dexosomes (FIG. 15). Interestingly, none of the spleens of mice spontaneously rejecting the tumor P815 or presenting P815 tumors exhibit this cytolytic activity under the same conditions. These results show that a single injection of dexosomes according to the invention derived from dendritic cells sensitized with an antigen or corresponding antigenic peptides is capable of triggering a specific CTL anti-tumor response in vivo efficaciously.

In order to determine whether the immune response and anti-tumor response induced by the dexosomes is restricted to the MHC and not simply due to a direct effect of the tumor peptides, dendritic cells derived from H2d (DBA/2) or H2b (C57BL/6) mice were loaded in parallel with tumor peptides eluted from the tumor P815. The dexosomes produced by these dendritic cells were then isolated and used separately for direct intradermal injections into the DBA/2 mice bearing established P815 tumors on day 6/10.

As is shown in FIG. 13B, only the dexosomes bearing the syngeneic tumor peptides are efficacious anti-tumor vaccines (inducing disappearance of the tumor iin 60%o of the mice) whereas the dexosomes of the allogeneic dendritic cells induce practically no anti-tumor effect. These results indicate that the dexosomes according to the invention induce an in vivo anti-tumor response restricted to the MHC.

Similar experiments to those described above were performed by giving intravenous rather than intradermal injections. The results obtained are presented in FIG. 16. They show first tumor regression following the intravenous injection of dexosomes. Furthermore, these results show that the dexosomes are more potent than the dendritic cells from which they are derived for eradicating tumors in vivo. These results thus illustrate the remarkable and unexpected properties of the dexosomes.

The results presented above thus show that the murine or human immature dendritic cells secrete dexosomes, that these dexosomes present not only class II molecules of the MHC but also class I molecules of the MHC as well as co-stimulatory molecules, and finally that these dexosomes are immunogenic and induce tumor regression in vivo.

These dexosomes may be obtained in relatively high quantities (1 μg per million dendritic cells per eighteen hours, according to the Bradford test) from dendritic cell culture medium (dendritic cells derived from bone marroow in the presence of GM-CSF+IL-4, D1 dendritic cell lines or dendritic cells derived from human monocyte precursors isolated from mononudeated cells from peripheral blood). The dexosomes were characterized biochemically and morphologically. The membrane vesicles analyzed by immunoelectron microscopy represent a homogeneous population of vesicles having a diameter of about 60 to 90 nanometers. The dexosomal preparations are apparent free of retrovirus, plasma membranes, microsomal constituents or apoptotic bodies. These dexosomes abundantly overexpress the molecules of classes I and II of the MHC, CD63 and CD86 in comparison to plasma membranes. No compartment derived from the endoplasmic reticulum was detected in the dexosomes by Western blotting, using anti-calnexin anntibodies. Programmed cell death could not be demonstrated in these cultures using different conditions. Interestingly, the production of these vesicles appears to be a regulated phenomenon. The quantity of vesicles seems to be able to be diminished by inducing maturation of the dendritic cells, as determined by the Bradford test, Western blotting and immuno-electron microscopy. Furthermore, the level of secretion of these vesicles may be improved significantly by lowering the pH of the culture medium or by incubating the cells in the presence of certain cytokines or even by subjecting the dendritic cells to irradiation treatment. This phenomenon is particularly unexpected in as much as the immature dendritic cells are usually considered to have a low potency of antigen presentation and hence a low immunological activity. The results presented show that it is the immature dendritic cells at this stage which possess the property of producing dexosomes efficaciously. The results presented show, finally, that these dexosomes are capable of triggering a response by efficacious T cells both in vitro and in vivo and that they are also capable of inducing tumor regression in vivo. Thus, these vesicles do indeed constitute particularly attractive candidates for immunotherapic approaches using non-cellullar systems.

11. Purification of Exosomes by Liquid Phase Electrophoresis

This example describes the use of an inventive purification method of exosomes based on liquid phase electrophoresis.

Liquid phase electrophoresis is a preparative method of separation of biological substances according to their charge. This method has been used to separate proteins by isoelectric focussing. This method may possess the following advantages:

it is a preparative method permitting continuous injection of material and hence the purification of large quantities of vesicles.

this method makes possible the purification of dexosomes in one or two steps, eliminating in principle the centrifugation steps.

In order to determine whether this method is applicable to the purification of exosomes, we have performed the following experiment:

A preparation of dexosomes isolated from a supernatant of murine dendritic cells by differential centrifugation was injected into liquid phase electrophoresis under the usual conditions described by Amigorena et al.(Nature, 369 (1994), 113). Forty fractions were collected and the protein concentration of each of these fractions was determined by the Bradford test (BioRad) in order to detect the presence of dexosomes. As is shown in FIG. 17, 90% of the dexosomes were found to be concentrated in four LPE fractions. The migration of the dexosomes as a narrow peak according to this technology demonstrates the practicability of the electrophoresis as a method of isolation of the dexosomes.

References

Amigorena, S., Drake, J. R., Webster, P. and Mellman, I. (1994) Transient accumulation of new class II molecules in a novel endocytic compartment in B lymphocytes (see comments) Nature, 369, 113–120.

Boczkowski, D., Nair, S. K., Snyder, D. and Gilboa, E. (1996). Dendritic cells pulsed with RNA are potent antigen-presenting cells in vitro and in vivo. Journal of Experimental Medicine 184, 465–72.

Boon, T. (1992). Towards a genetic analysis of tumor rejection antigens. Advances in Cancer Research 58, 177–210.

Espevik, T. & Nissen-Meyer, J. (1986) J. Immunol. Methods 95: 99–103.

Felder, S., Miller, K., Moehren, G., Ullrich, A., Schlessinger, J. and Hopkins, C. R. (1990). Kinase activity controls the sorting of the epidermal growth factor receptor within the multivesicular body. Cell 61, 623–634.

Mayordomo, J. I., Zorina, T., Storkus, W. J., Zitvogel, L., Celluzzi, C., Palo, L. D., Melief, C. J., Ildstad, S.T., Kast, W. M., Deleo, A. B. et al. (1995). Bone marrow-derived dendritic cells pulsed with synthetic tumour peptides elicit protective and therapeutic antitumour immunity. Nature Medicine 1, 1297–1302.

Nabel, C. J., Gordon, D., Bishop, D. K., Nicholoff, B. J., Yang, Z. Y., Avuga, A., Cameron, M. J., Nabel, E. G., Chang, A. E. (1996). Immune response in human melanoma after transfer of an allogenic class I major histocompatibility complex gene with DNA-liposome complexes. Proc. Natl. Acad. Sci. USA 93: 15388–15393.

Pardoll, D. M. (1995). Paracrine cytokine adjuvants in cancer immunotherappy. Annual Review of Immunology 13, 399–415.

Raposo, G., Nijman, H. W., Stoorvogel, W., Leijendekker, R., Harding, C. V., Melief, C. J. M. and Geuze, H. J. (1996). B lymphocytes secrete antigen-presenting vesides. J. Exp. Med. 183, 1161–1172.

Rosenberg, S. A., Kawakami, Y., Robbins, P. F. and Wang, R. (1996). Identification of the genes encoding cancer antigens: implications for cancer immunotherapy. Advances in Cancer Research 70, 145–77.

Traversasi, C., Van der Bruggen, P., Leuscher, I. F., Lurguin, C., Chamez, P., Van Del, A., De Places, E., Amar-Costesec, A. and Boon, T. (1992). A nonapeptide encoded by human gene MART-1 is recognized on HLA-A1 by cytotoxic T lymphocytes directed against tumor antigen MZ2-E. J. Exp. Med. 176: 1453–1457.

Walker, S. A. et al. (1997). Nature, vol. 387, pp. 61 et seq.

Zitvogel, L., Robbins, P. D., Storkus, W. J., Clarke, M. R., Maeurer, M. J., Campbell, R. L., Davis, C. G., Tahara, H., Schreiber, R. D. and Loze, M. T. (1996). Interleukin-12 and B7.1 co-stimulation cooperate in the induction of effective antitumor immunity and therapy of established tumors. European Journal of Immunology 26, 1335–41 (a).

Zitvogel, L., Mayordomo, J. I., Tjandrawan, T., Deleo, A. B., Clarke, M. R., Lotze, M. T. and Storkus, W. J. (1996). Therapy of murine tumors with tumor peptide-pulsed dendritic cells: dependence on T cells, B7 costimulatory and T helper cell 1-associated cytokines (see comments). Journal of Experimental Medicine 183, 87–97 (b).

TABLE 1

Production of texosomes by human and murine tumor cell lines.

| TUMOR CELL LINES | TEXOSOMES ($\mu G/2 \times 10^7$ CELLS/18 H) |
| --- | --- |
| Murine tumors | |
| MCA101 | 172 |
| P815 | 163 |
| MC38 | 120 |
| L1210 | 150 |
| TS/A | 160 |
| Human (melanomas) | |
| VIO* | 80 |
| FON | 90 |
| MZ2-2 | 18 |
| Human (nephromas) | |
| RCC NUN* | 120 |
| RCC JOUA* | 18 |
| RCC MEG* | 10 |
| RCC GIAM* | 100 |

What is claimed is:

1. A method for producing isolated immunogenic membrane vesicles comprising the steps of:

(i) culturing human monocyte precursor cells in the presence of a combination of cytokines to produce a population of cells comprising human immature dendritic cells;

(ii) culturing said population of cells under conditions allowing a release of membrane vesicles by said immature dendritic cells, said conditions comprising conditions wherein said population of cells is subjected to at least one treatment selected from the group consisting of incubation in the presence of a cytokine favoring the immature state, irradiation, and reduction of the pH of the culture; and (iii) isolating membrane vesicles released from said cells, said vesicles being imnmunogenic.

2. The method of claim 1, wherein in step (i), said combination of cytokines comprises GM-CSF and a cytokine selected from the group consisting of IL-4 and IL-13.

3. The method of claim 1, wherein in step (ii), said cytokine is selected from the group consisting of gamma interferon, interleukin-10, and interleukin-12.

4. The method of claim 1, wherein during step (ii), said immature dendritic cells arc contacted with an antigen, thereby producing membrane vesicles comprising said antigen.

5. The method of claim 1, further comprising the step of purifying said vesicles by a process comprising centrifugation or liquid phase electrophoresis.

* * * * *

UNITED STATES PATENT AND TRADEMARK OFFICE
CERTIFICATE OF CORRECTION

PATENT NO.   : 6,685,911 B1
DATED        : February 3, 2004
INVENTOR(S)  : Laurence Zitvogel et al.

It is certified that error appears in the above-identified patent and that said Letters Patent is hereby corrected as shown below:

<u>Title page, Item [54] and Column 1, lines 1-3,</u>
Title, delete "SENSITIZATION PROCESS FOR ANTIGEN-PRESENTING CELLS AND MEANS FOR IMPLEMENTING THE PROCESS" and replace with -- PRODUCTION OF ISOLATED MEMBRANE VESICLES --.

Signed and Sealed this

Eighteenth Day of May, 2004

JON W. DUDAS
*Acting Director of the United States Patent and Trademark Office*